(12) United States Patent
Taylor

(10) Patent No.: US 10,449,341 B2
(45) Date of Patent: Oct. 22, 2019

(54) FACE SOAKING DEVICE

(71) Applicant: John Richard Taylor, Arp, TX (US)

(72) Inventor: John Richard Taylor, Arp, TX (US)

( * ) Notice: Subject to any disclaimer, the term of this patent is extended or adjusted under 35 U.S.C. 154(b) by 0 days.

(21) Appl. No.: 15/581,919

(22) Filed: Apr. 28, 2017

(65) Prior Publication Data

US 2017/0232242 A1     Aug. 17, 2017

Related U.S. Application Data

(63) Continuation-in-part of application No. 14/964,552, filed on Dec. 9, 2015, and a continuation-in-part of application No. 14/877,856, filed on Oct. 7, 2015.

(Continued)

(51) Int. Cl.
*A61M 35/00* (2006.01)
*A62B 18/00* (2006.01)
*A61N 5/06* (2006.01)

(52) U.S. Cl.
CPC ........... *A61M 35/00* (2013.01); *A61N 5/0616* (2013.01); *A62B 18/00* (2013.01); *A61M 2202/04* (2013.01); *A61M 2202/0468* (2013.01); *A61M 2205/051* (2013.01); *A61M 2205/36* (2013.01); *A61M 2207/00* (2013.01); *A61M 2210/0606* (2013.01); *A61N 2005/0626* (2013.01);
(Continued)

(58) Field of Classification Search
CPC ....................................................... A45D 19/00
USPC ..................................................... 4/621, 555
See application file for complete search history.

(56) References Cited

U.S. PATENT DOCUMENTS 1,446,841 A    2/1923  Dietsche
2,475,259 A    4/1949  Singleton
(Continued)

FOREIGN PATENT DOCUMENTS

EP    0930033 A1    7/1999
EP    2868218 A1    6/2015
(Continued)

OTHER PUBLICATIONS be26-minimal-circle-blur-art-illusion, posted at androidpapers.co, online URL:http://androidpapers.co/be26-minimal-circle-blur-art-illustration/ (Year: 2019).

(Continued)

*Primary Examiner* — Lauren A Crane
(74) *Attorney, Agent, or Firm* — Eric Kelly

(57) ABSTRACT

Face soaking devices (devices) and methods of use are described and disclosed. In some embodiments the device may comprise a vessel and a vessel neck gasket. The vessel may be configured to hold a liquid to submerge a face of a user or a portion thereof. The vessel neck gasket may be (removably) joined to the vessel. The vessel neck gasket may be configured to comfortably accommodate a portion of the user's neck. In some embodiments, the device may comprise a breathing apparatus that may be in removable contact with: the vessel, with a head rest subassembly, and/or with the user. The breathing apparatus may be configured to permit the user to breathe while the user's face may be submerged within the liquid. When the vessel may be filled with the liquid to at least a sufficient level, the user may soak the face or the portion thereof, such that the skin being soaked receives a benefit.

19 Claims, 29 Drawing Sheets

Related U.S. Application Data

(60) Provisional application No. 62/351,830, filed on Jun. 17, 2016.

(52) U.S. Cl.
CPC ............ *A61N 2005/0643* (2013.01); *A61N 2005/0651* (2013.01); *A61N 2005/0652* (2013.01)

(56) References Cited

U.S. PATENT DOCUMENTS

| | | |
|---|---|---|
| 3,465,370 A | 9/1969 | Chernick |
| 3,733,620 A | 5/1973 | Glintz |
| 4,004,302 A | 1/1977 | Hori |
| D249,278 S | 9/1978 | Milligan |
| 4,152,792 A | 5/1979 | Glintz |
| 4,281,423 A | 8/1981 | Fukunaga |
| 4,546,504 A | 10/1985 | Vars |
| 4,561,979 A | 12/1985 | Harms |
| 4,649,580 A | 3/1987 | Bastien |
| 4,864,667 A | 9/1989 | Adams |
| 5,245,713 A | 9/1993 | Tickle |
| 5,381,562 A | 1/1995 | Holloway |
| D396,982 S | 8/1998 | Harris |
| D398,075 S | 9/1998 | Book |
| 6,328,031 B1 | 12/2001 | Tischer |
| 6,405,389 B1 | 6/2002 | Harty |
| D461,278 S | 8/2002 | Takechi |
| 6,558,344 B2 | 5/2003 | McKinnon |
| 6,609,257 B1 | 8/2003 | O'Geary |
| D483,493 S | 12/2003 | Lie |
| D491,670 S | 6/2004 | Leung |
| D495,059 S | 8/2004 | Lie |
| D500,893 S | 1/2005 | Chang |
| D522,174 S | 5/2006 | Jackel-Marken |
| D551,513 S | 9/2007 | Fiorella |
| D566,246 S | 4/2008 | Cunningham |
| D573,260 S | 7/2008 | Dunshee |
| 7,448,093 B1 | 11/2008 | Ruck |
| D583,958 S | 12/2008 | Usui |
| 7,641,835 B2 | 1/2010 | Ramsey |
| D621,927 S | 8/2010 | Dominguez |
| 7,785,303 B2 | 8/2010 | Tapadiya |
| D632,798 S | 2/2011 | Tran |
| 7,931,157 B1 | 4/2011 | Palumbo |
| D638,170 S | 5/2011 | Chen |
| D672,086 S | 12/2012 | Tai |
| 8,375,478 B2 * | 2/2013 | Luo ................... E05B 17/0025 292/139 |
| D692,149 S | 10/2013 | Uematsu |
| D707,997 S | 7/2014 | English |
| D712,558 S | 9/2014 | Ledbetter |
| D715,002 S | 10/2014 | Chang |
| D716,958 S | 11/2014 | Thomas |
| D736,939 S | 8/2015 | McKay |
| D736,940 S | 8/2015 | McKay |
| D757,280 S | 5/2016 | Ogaki |
| D757,282 S | 5/2016 | Loyd |
| D767,154 S | 9/2016 | Bromilow |
| 9,669,519 B2 | 6/2017 | Wunderlich |
| D809,804 S | 2/2018 | Tai |
| D831,838 S | 10/2018 | Koifman |
| D837,542 S | 1/2019 | Nicoll |
| 2002/0146955 A1 | 10/2002 | Levine |
| 2004/0025243 A1 | 2/2004 | Chien |
| 2004/0225265 A1 | 11/2004 | Tapadiya |
| 2008/0234610 A1 | 9/2008 | Summers |
| 2010/0006467 A1 | 1/2010 | Joseph |
| 2011/0225726 A1 | 9/2011 | Dominguez |
| 2012/0222210 A1 | 9/2012 | Wiggins |
| 2012/0227177 A1 | 9/2012 | Kiser |
| 2013/0053737 A1 | 2/2013 | Scerbo |
| 2014/0073996 A1 | 3/2014 | Jaguan |
| 2015/0305573 A1 | 10/2015 | Stafford |
| 2015/0328393 A1 | 11/2015 | Stephens |
| 2016/0213562 A1 * | 7/2016 | Gathers ............. A61H 35/00 |

FOREIGN PATENT DOCUMENTS

| | | |
|---|---|---|
| FR | 2637180 A1 | 6/1990 |
| JP | 558358 S | 4/1981 |
| JP | 1367329 | 8/2009 |
| JP | 1367331 | 8/2009 |
| WO | 2009094601 A2 | 7/2009 |

OTHER PUBLICATIONS

CNBTR 5PCS 88mm Universal HCS Flat Semicicle Saw Blades Black, posted at aliexpress.com, online, URL:https://www.aliexpress.com/item/CNBTR-5PCS-88mm-Universal-HCS-Flat-Semicircle-Saw-Blades-Black/32777274663.html (Years: 2019).

Find the area of shaded region in Fig. 1248, where arc(APD, AQB, BRC, and CSD) are semicircles, posted Feb. 8, 2018, posted at sarthaks.com, online, URL:https://www.sarthaks.com/32495/find-the-area-of-the-shaded-region-in-fig-12-48-where-arc-apd-brc-and-csd-are-semicircles (Year: 2018).

* cited by examiner

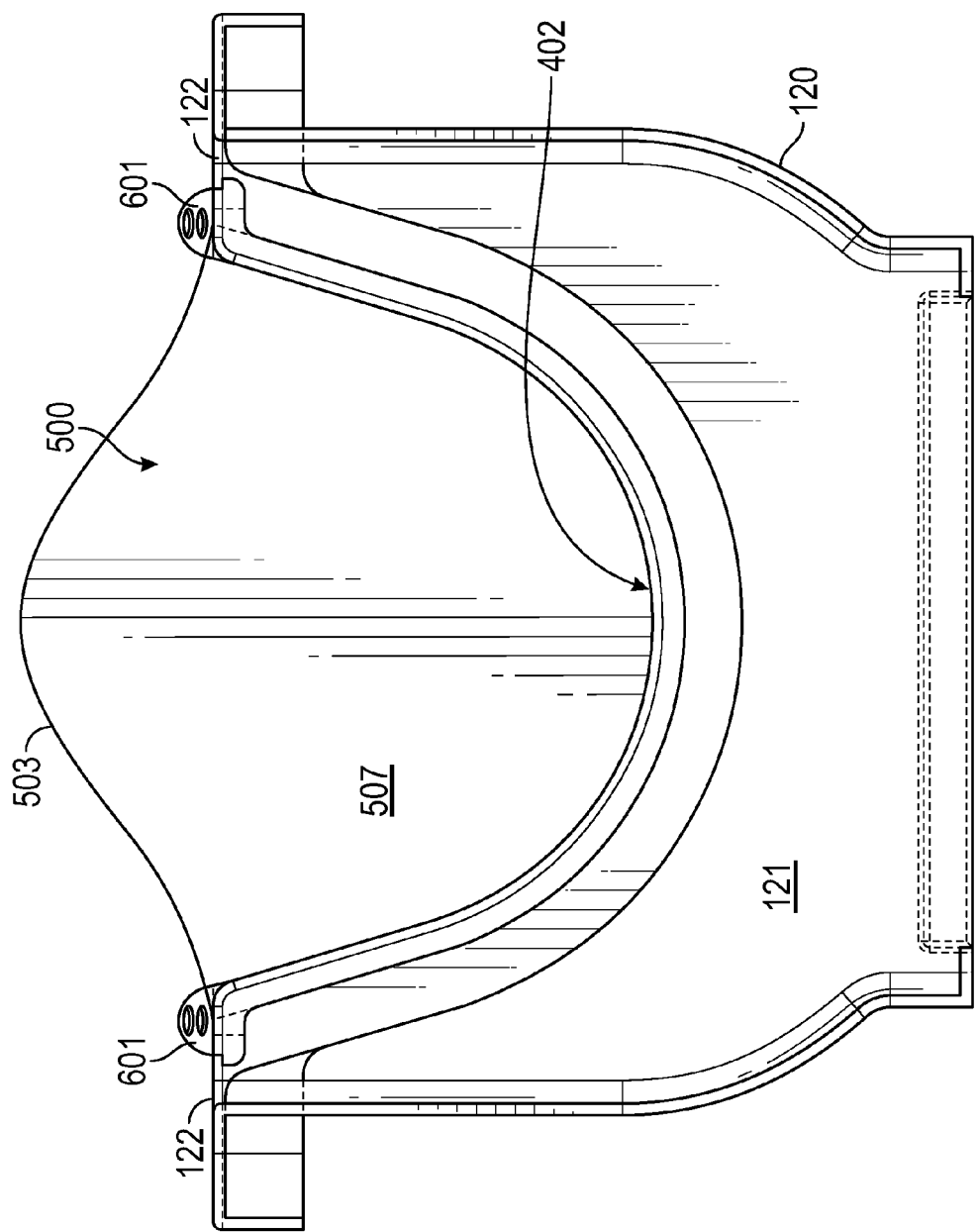

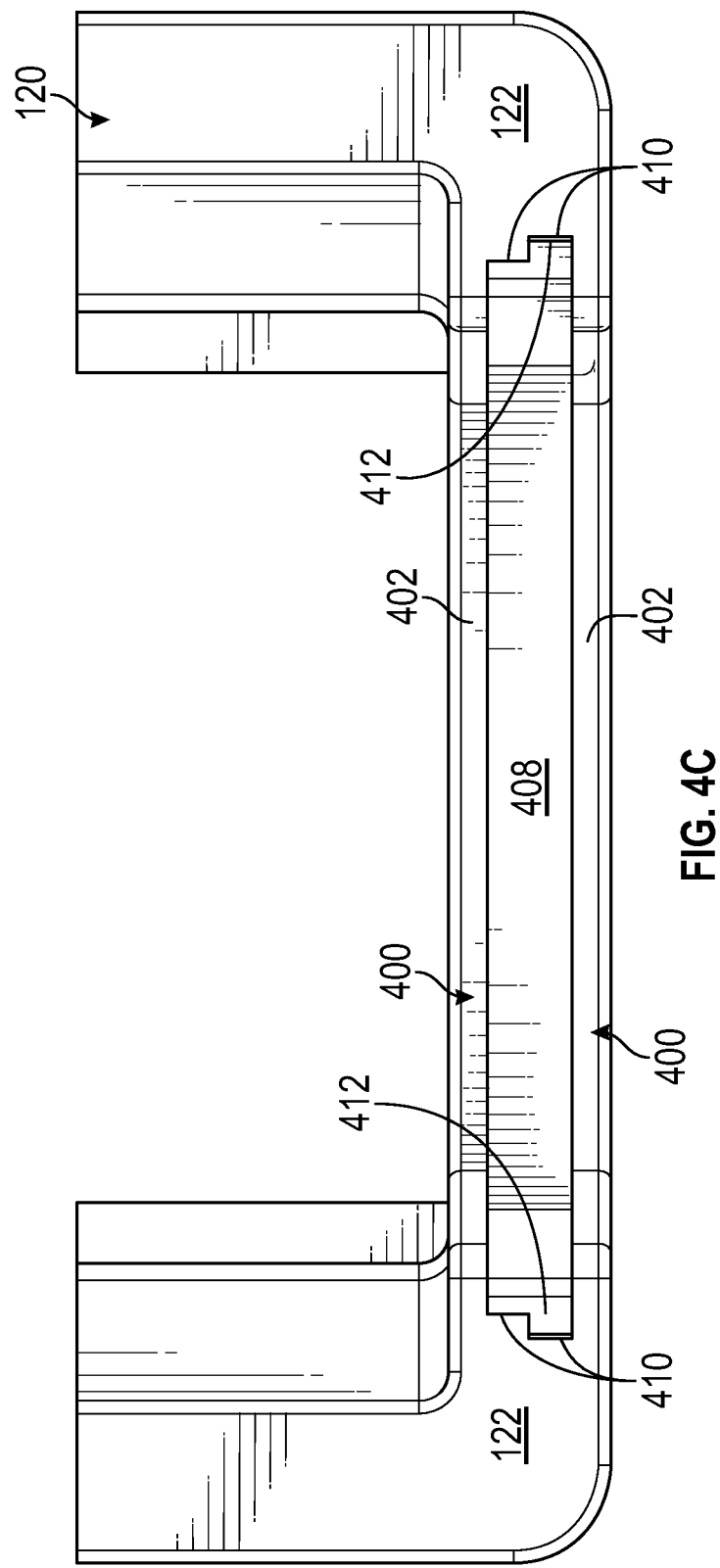

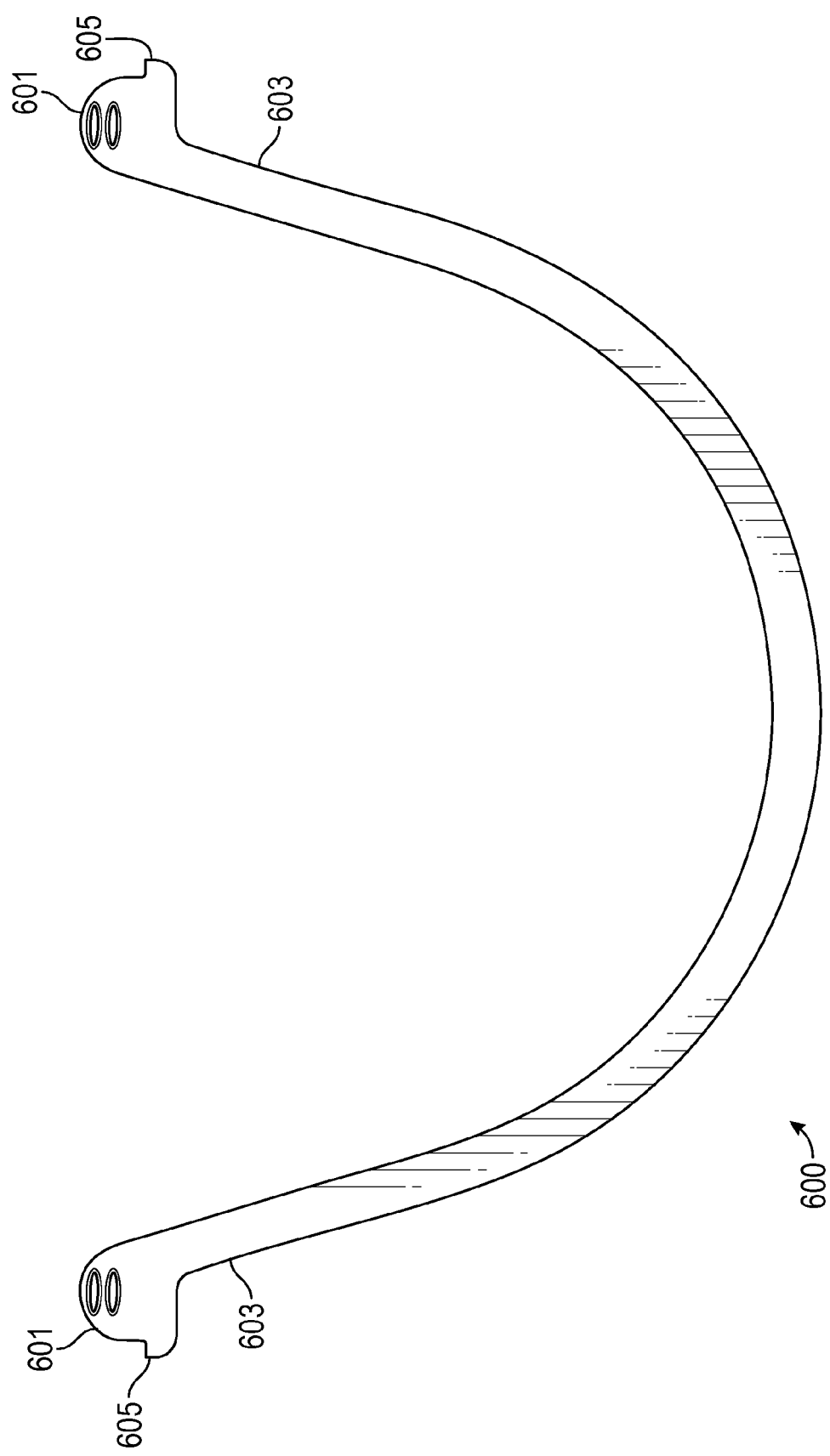

FACE SOAKING DEVICE

PRIORITY NOTICE

The present application claims priority under 35 U.S.C. § 119(e) to U.S. provisional patent application, application No. 62/351,830 filed on Jun. 17, 2016, the disclosure of which is incorporated herein by reference in its entirety.

The present patent application is a continuation-in-part (CIP) of U.S. non-provisional patent applications: application Ser. No. 14/877,856 filed on Oct. 7, 2015; and application Ser. No. 14/964,552 filed on Dec. 9, 2015; wherein this present patent application claims priority to both said U.S. non-provisional patent applications under 35 U.S.C. § 120. The above-identified parent U.S. non-provisional patent applications are incorporated herein by reference in their entirety as if fully set forth below.

The present patent application is a continuation-in-part (CIP) of patent application, application number PCT/US15/54576, filed on Oct. 7, 2015; wherein this present patent application claims priority to said PCT non-provisional patent application.

CROSS REFERENCE TO RELATED PATENT APPLICATIONS

The present application is related to presently pending filed patent application, application number PCT/US15/54576, filed on Oct. 7, 2015; wherein said presently pending PCT patent application is incorporated by reference in its entirety.

TECHNICAL FIELD OF THE INVENTION

The present invention relates in general to skin soaking devices and more specifically to face soaking devices.

COPYRIGHT AND TRADEMARK NOTICE

A portion of the disclosure of this patent application may contain material that is subject to copyright protection. The owner has no objection to the facsimile reproduction by anyone of the patent document or the patent disclosure, as it appears in the Patent and Trademark Office patent file or records, but otherwise reserves all copyrights whatsoever.

Certain marks referenced herein may be common law or registered trademarks of third parties affiliated or unaffiliated with the applicant or the assignee. Use of these marks is by way of example and should not be construed as descriptive or to limit the scope of this invention to material associated only with such marks.

BACKGROUND OF THE INVENTION

The skin (epidermis) of humans (and of terrestrial vertebrates) may suffer from a number of problems, such as: acne; wrinkles, including age spots; infections; physical damage; various rashes, including *pityriasis rosea*, acne rosacea; and the like. Each of these skin problems may be briefly discussed below.

Acne may result from clogged skin pores, which may be visible as pustules or pimples—i.e., what are commonly called blackheads and whiteheads. Such visible acne may be both visually unpleasant and painful. Severe acne may also result in scaring from the physical damage associated with ruptures of follicle walls, which may also form deep cysts under the skin. The clogged skin pores visible as acne may result from an overproduction of sebum oil, keratin, and/or metabolic byproducts of skin pore bacteria, as well as from the cells of skin pore bacteria. A common skin pore bacterium is *Propionibacterium acnes* (*P. acne*).

Undesirable wrinkles on the skin may result from age, environmental factors, genetic factors, and repeated facial expressions. Age may be a factor in wrinkle formation because as skin ages, it may lose elasticity, in part due to accumulated gravitational pull over time and changes in connective tissues. Additionally with age, sebum production may slow (from the sebaceous glands), which may contribute to skin dryness with age, wherein such skin dryness may enhance visibility of wrinkles. Environmental factors may include sun and wind exposure as well as exposure to smoke, which over time may also contribute to wrinkles. Further, consistent facial expressions over time such as squinting, smiling, and even thinking can result in skin wrinkles. And in addition to wrinkles, age spots, such as liver spots and solar lentigines may also appear on the skin as the skin ages and is exposed to various environmental factors over time.

Additionally, various microorganisms, which may include bacteria, fungi, protozoans, and even some small invertebrates may infect skin, both on the surface and within the skin tissue, with varying levels of severity. For example, the mere presence of some such microorganisms, whether dead or alive, may act as an irritant, causing inflammation. Some microorganism metabolic byproducts may also act as irritants; whereas, some byproducts may actually be toxic. And some microorganisms may actually feed on the skin itself and/or the natural secretions of the skin, such as sebum. Such microorganisms may also infect open wounds on the skin and use such open wounds to gain entry to the body, and pose a larger bodily infectious threat.

Additionally, viruses may cause contagious, painful, and/or unpleasant looking lesions and blisters, e.g., cold sores. Such lesions and blisters if ruptured may result in physical damage to the skin, as well as pain. Such viruses may include herpes and herpes like viruses.

With respect to physical damage to the skin, this may include: various wounds, cuts, abrasions, burns, lesions, blisters, ruptures, and the like. Such physical damage to the skin may result in scarring as the skin heals and prior to healing may increase chances for various microorganism infection.

Such skin problems, particularly when occurring on the face, because of the inherent visibility to others of the face, may result in collateral detrimental effects, such as to one's psychological, social, and occupational wellbeing.

*Pityriasis rosea* may be a type of skin rash. Often, *pityriasis rosea* may begin with a single "herald patch" an oval red lesion of 2 to 10 centimeters (cm), followed in one or two weeks by a generalized body rash of many small (5 to 10 millimeter (mm)) patches of pink and/or red, flaky, oval shaped lesions, which often appear on the torso, but may also appear on the cheeks and/or at the hairline.

Acne rosacea or just rosacea may be a chronic skin rash condition characterized by facial erythema (redness) and sometimes pimples. Rosacea may affect all ages. Rosacea may typically begin as redness on the central face across the cheeks, nose, or forehead, but may also affect the neck, chest, ears, and/or scalp. In some cases, additional signs, such as semi-permanent redness, telangiectasia (dilation of superficial blood vessels on the face), red domed papules (small bumps) and pustules, red gritty eyes, burning and stinging sensations, and in some advanced cases, a red lobulated nose (rhinophyma), may be present.

The prior state of the art has responded to such problems with a diversity of technologies. For example, there may be a plethora of various topical ointments and creams for treating various skin problems. However, relevant here, may be the application of soaking the affected skin in an immersion liquid. Regardless of explanation, the prior state of art has shown a positive correlation with improvements to the above noted skin problems with soaking the skin in an appropriate immersion liquid. For example, such a treatment modality may be known in the art generally as hydrotherapy when the immersion liquid in question may be predominantly water. However, such hydrotherapy principles may be applied to other such immersion liquids, such as various oils, various paraffin waxes (typically heated), and oil water mixtures (emulsions). As used herein, hydrotherapy may be a means of treating various skin problems, by immersing the skin in a particular immersion liquid, wherein the immersion liquid may be predominantly water or some other liquid, such as an oil in liquid form at room temperature or an appropriate temperature, such as paraffin wax in liquid form when appropriately heated, or an oil and water mixture.

Such hydrotherapy may involve soaking a target region of skin within the immersion liquid. The immersion liquid may comprise various properties. For example, the immersion liquid may contain various dissolved salts, wherein such a liquid may be known herein as a saline solution. For example, the immersion liquid may contain released oxygen, either as dissolved oxygen and/or as gas bubbles within the immersion liquid. For example, the immersion liquid may contain an increased or decreased temperature with respect to room temperature. And for example, the immersion liquid may be directed via one or more jets, such that a stream of liquid pressure may be directed at the target region of skin.

With respect to saline solutions as the immersion liquid, saline and salts as used herein may refer not only to solutions of sodium chloride, but may also refer to other minerals in solution, e.g. potassium and/or magnesium, that may be dissolved in a solvent, such as predominantly water. Various negative ions, such as chloride, may also be present in solution with the positive mineral ions. For example, sodium and potassium salt solutions may be present with chloride ions and magnesium may be present with sulfate ions, as in Epsom salt. An immersion liquid using various salts may promote different benefits. For example, some such saline solutions may soften the skin and/or others may tend to moisturize the soaked skin.

Benefits to the skin from soaking the skin in saline solutions may predominantly function by osmosis. Osmosis is a random movement of water molecules across partially-permeable membranes (such as cellular membranes, including skin cells), from an area of high water concentration (e.g. within a cell) to an area of low water concentration (e.g. the saline solution). Thus osmosis will function to draw water out of cells, including skin cells, when the saline solution has a salinity that is greater than the salinity within the cells. For example, human blood has an average salinity of about 0.85% by weight, which is often rounded to 0.9%. Thus if the saline solution that the skin may be soaking in is greater than 0.9% by weight, there will be osmotic flow of water molecules from the skin cells into the saline solution.

However, it is from this flow of water molecules across cell membranes that several benefits may result for treating and/or improving the various skin problems noted above.

For example, with respect to acne, skin with acne that is exposed to saline solutions may see a reduction in acne. Such reduction may result from the saline solution reducing sebum oil within pores, by the saline solution reducing the population of skin pore bacteria, and/or by the saline solution encouraging a reduction in skin pore size. The saline solution may help to loosen sebum oil from pores. With respect to skin pore bacteria, which may be adapted for non-saline environments, such bacteria may not be adapted to cope with the osmotic flow of water molecules out of the bacterial cells. Such saline solutions may hinder reproduction of such bacterial cells. Such saline solutions may actually kill such bacterial cells. With respect to the reduction in skin pore size, this may also result from osmotic flow of water molecules.

With respect to a reduction in wrinkles, the saline solution may reduce wrinkles by softening the wrinkled skin tissue and by stimulating the sebaceous glands to produce sebum oil which may combat age associated skin dryness. For example, exposing a face to warm water may soften facial skin in preparation and aiding in shaving whiskers (stubble) from that face. Additionally, depending upon the salinity of the given saline solution, the saline solution may have a hydrating effect upon the immersed skin.

With respect to mitigating against microorganism infection of the skin, as noted above, those microorganisms which may be predominantly present on the skin are not typically adapted to withstand osmotic flow of water molecules from within the bacterial cells. Immersion of skin in such saline solutions may result in microorganism population reduction.

With respect to improving a rate of healing damaged skin, skin immersed into saline solutions may experience an improved rate of healing by reducing the populations of microorganisms which may interfere with healing. And the osmotic flow may also aid healing damaged skin by aiding transport of nutrients and repair proteins from within the cells and tissues below the surface skin to the damaged skin site.

Thus immersion of skin into a saline solution which may have a salinity greater than the skin tissue being immersed, may result in a plurality of benefits to the immersed skin.

Now turning to oxygen treatments for the skin and how oxygen may reduce some of the skin problems identified above. Again, regardless of explanation, the state of the prior art shows a positive correlation with exposing skin to oxygen and improvements in the skin.

Molecular oxygen (atmospheric oxygen), i.e. $O_2$, may be essential for cellular respiration and the basis for how each vertebrate cell derives energy via the Krebs Cycle (Citric Acid Cycle). Without a sufficient supply of consistent oxygen to any vertebrate cell, that cell may be hypoxic and may have a diminished capacity to operate normal cellular activities, including a diminished capacity to reproduce, to fight infection, and/or to heal. By providing oxygen in sufficient concentration directly to the skin, such exposed skin may obtain some of its needed oxygen directly, instead of relying largely upon delivery of oxygen via hemoglobin in red blood cells. Such skin cells having a steady available source of oxygen may allow such skin cells a full range of normal cellular activities. Additionally, immune system cells (e.g. macrophages and phagocytes) which target and kill infectious microorganisms better perform when such cells have an adequate supply of oxygen. And a second mechanism of oxygen reducing infectious microorganism population may be by oxygen's oxidation properties and ability to form reactive oxygen species that may then oxidize bacterial cellular machinery, such as interfering with bacterial cell walls.

Now oxygen may be applied to the skin in gaseous form and/or released as a dissolved gas and/or as gas bubbles within a liquid, including the immersion liquid. For example, atmospheric air will contain atmospheric oxygen, e.g. at approximately 20.95%. A delivered concentration of gaseous oxygen may be increased over the atmospheric percentage by using pure oxygen as a supply source. However, use of gaseous oxygen directed at skin may have the drawback of being difficult to control and manipulate due to the gasses' inherent ability to more freely and disperse. Whereas, release of oxygen in a liquid may provide for better control as the target area of skin may be immersed in the liquid, which then may have oxygen from air or pure oxygen released into the liquid.

The benefits of oxygen and saline solutions may be combined into the same immersion liquid. For example, air (which includes oxygen) and/or oxygen may be pumped or released into an appropriate saline solution. Additionally, such an oxygenated saline solution may be combined with the benefits of controlling a temperature of the oxygenated saline solution.

For example, increasing a temperature of the immersion liquid above room temperature but less than a temperature which may be harmful (e.g. painful), allows for an increase in chemical reactions (kinetics). Thus increasing the immersion liquids temperature in such a range will tend to increase the effectiveness of saline solutions as well as the effectiveness of oxygenation of the skin. Additionally, such increased temperature of the immersion liquid may result in an environment that may be soothing and relaxing to a user. Such a soothing and relaxing result may then release stress and mitigate against headaches. Release of stress may promote lowering of blood pressure, healing of damaged skin, and a stronger immune system. Thus, increasing the temperature of the immersion liquid not only may provide direct improvements to how the saline and the oxygen functions to improve the skin, but by creating the soothing and relaxing environment, a collateral benefit of stress release may be achieved, which may also then include a cascade of additional benefits.

Further, increasing the immersion liquids temperature above room temperature may then permit the immersion liquid to be used for heat therapy. Heat therapy may be used to treat not only skin problems, but also other ailments, such as, but not limited to, arthritis, osteoarthritis, fibromyalgia, joint stiffness, bursitis, tendonitis, sprains and pulled muscles. The heat and immersion liquid which may convey the heat, may increase blood flow, improve joint stiffness and reduce pain. For example, heated paraffin waxes as the immersion liquid may be utilized. Such heated paraffin wax may soften hardened skin caused by scleroderma, a disease in which collagen accumulates on the body.

In addition or alternatively, decreasing the immersion liquids temperature below room temperature may then permit the immersion liquid to be used for cold therapy. Chilling the liquid by use of a chiller, chilling equipment, and/or by introduction of ice, may then permit various cold therapies to be used to treat the face or other body part which may be removably immersed into the chilled liquid. Additionally or alternatively, heat therapy may be alternated with cold therapy; wherein such alternation of warmth and cold may aid in increasing blood flow, facilitating removal of cellular toxins (e.g., but not limited to, lactic acid), and/or promoting healing of burned or traumatized tissue.

Additionally, liquid jets, for example water jets, when directed at the immersed skin may also result in an environment that is soothing and relaxing to the user. Such water jets also may have their benefit increased when the immersion temperature is increased as noted per above.

Light therapy may also be used to impart various benefits to the exposed skin and/or body in general. Light therapy may involve directing a source of light at skin. Some wavelengths of light have found to increase healing rates of damaged skin, such damaging including cuts, scrapes, bruising, lacerations, lesions, and the like. Light such as ultraviolet (UV) light may also be used for skin tanning purposes. However, both existing oxygen therapy and existing light therapy are conducted in a treatment environment of atmospheric air, i.e., not with an article to be treated (e.g. a region of skin) submerged within an immersion liquid.

Additionally, it may be desirable to expand beyond just oxygen, air, or air enriched with oxygen, as treatment gasses for skin.

Additionally, current light therapy devices generally are directed at emitting only a very narrow range of wavelengths, generally within the visible light spectrum, near infrared (IR), and near ultraviolet (UV). It would be desirable to have expanded devices that may be capable of emitting electromagnetic (EM) radiation in various wavelengths that may encompass regions of the entire EM spectrum, i.e. not necessarily a single device capable of emitting across the entire EM spectrum (since different technologies may be required to produce a given range of wavelengths), but rather a multitude of EM emitting devices where each different device may be capable of emitting a particular range of wavelengths, such that these different EM emitting devices may collectively be able to cover the entire EM spectrum.

Conducting oxygen therapy and/or light therapy or other EM therapy within the immersion liquid may be desirable for several reasons. Because the liquid is more dense than atmospheric air, more control over directing oxygen (or other gas) to a target region on the article (e.g., immersed skin region) may be achieved over conducting oxygen therapy in atmospheric air, where expelled oxygen quickly dissipates into the atmospheric air. By using the immersion liquid to removably submerge the target region of the article, useful properties of the liquid may be tailored for specific applications with respect to the target region of the article. For example, liquid water, such as saline solutions, may soften the skin and make such softened skin better able to benefit from exposure to oxygen and/or various wavelengths of light. The additives in the liquid may be used to heal, cleanse, rejuvenate, sanitize, sterilize, and the like. Likewise, controlling a temperature of the liquid may then be able to impart heat or withdraw heat from the target region of the article in a much greater efficiency than may be possible where the treatment environment is atmospheric air and not the liquid. Additionally, controlling the temperature (up, down, or maintaining) of the liquid may increase or decrease the efficacy of the additives, e.g., from a kinetics perspective.

Furthermore, it has been discovered that conducting light therapy or other EM therapy may be enhanced when the EM radiation may be emitted through a plurality of bubbles within the immersion liquid, by providing an increased coverage of the target region of the article receiving EM radiation in comparison to if there were no bubbles. The emitted EM radiation and the bubbles produce an optical chain reaction (OCR) phenomena that provides this enhancement.

However, as noted above, with respect to such skin problems on the face, these problems are exacerbated because the high visibility of the face. Additionally, these skin problems on the face are exacerbated because the current state of the art does not provide a means by which the user may immerse the face to receive hydrotherapy, wherein the hydrotherapy immersion liquid may comprise saline solutions, delivery of oxygen (and/or other gasses), heating means for increasing and/or decreasing immersion liquid temperature, and/or use of liquid jets. The problem that the prior state of the art has failed to address, until this invention, results from two biological facts. One, terrestrial vertebrates breathe from their nose and/or mouth located on the face and thus a hydrotherapy means for the face needs to provide a means by which the user may breathe while the user's face is immersed. Otherwise immersion of the face is limited to how long the user can hold their breath. And two, all pre-existing vessels have no means to accommodate a neck region of the user, particularly the soft tissue regions of the neck (front and sides of the neck), so if the user were to submerge the user's face into a pre-existing vessel, a rim of that vessel would press into the neck region causing discomfort rendering the prior state of the art ineffective for hydrotherapy of the face. Or the user would have to angle their head into the prior art vessel and attempt to hold their head at an uncomfortable angle to soak their face, which if is prolonged may result in neck pain. Additionally, it may be desirable if such a device might, in at least some embodiments, comfortably support the head region of the user, particularly the forehead, to promote facial immersion that may be comfortable and not strain the neck; wherein the user may soak their face, in comfort, for extended periods of time.

There is a need in the art for devices and/or methods that permit treating specifically targeted regions of the articles (e.g., skin) to be removably submerged in the immersion liquid and then treated with various gas bubbles, such as oxygen, treated with various wavelengths of EM radiation, such as visible light, and/or providing for an enhanced EM radiation coverage of the treated region by a synergistic combination of EM radiation and bubbles that may result from directing EM radiation through bubbles in the liquid.

There then is a need in the art for a device which may promote comfortable face immersion into the immersion liquid that both allows the user to breathe while the face is immersed and that may be comfortable to the neck of the user.

It is to these ends that the present invention has been developed.

BRIEF SUMMARY OF THE INVENTION

To minimize the limitations in the prior art, and to minimize other limitations that will be apparent upon reading and understanding the present specification, one or more embodiments of the present invention may describe a face soaking device.

Some embodiments may provide for a device which may be used to place and hold a person's face into a liquid for an extended time while the person conveniently and/or comfortably breathes through a breathing tube (e.g., a breathing apparatus). While the person has his or her face immersed in the liquid, the device may aerate the liquid (with various gasses). In some embodiments, the device may be designed to minimize or prevent the spillage of liquid onto the person's clothing or the immediate area around the device.

In some embodiments the face soaking device may comprise a vessel and a vessel neck gasket. The vessel may be configured to hold a liquid to submerge a face of a user or a portion thereof. The vessel neck gasket may be removably joined to the vessel. The vessel neck gasket may be configured to comfortably accommodate a portion of the user's neck. In some embodiments, the face soaking device may also comprise a breathing apparatus that may be in removable contact with: the vessel, with a head support, and/or with the user. The breathing apparatus may be configured to permit the user to breathe while the user's face (in whole or in part) may be submerged within the liquid. When the vessel may be filled with the liquid to at least a sufficient level, the user may soak the face or the portion thereof, such that skin being soaked receives a benefit.

It is an objective of the present invention to provide a face soaking device that may be used to reduce severity of facial acne by immersing the face within the immersion liquid.

It is another objective of the present invention to provide the face soaking device that may be used to reduce severity of facial wrinkles and/or facial age spots by immersing the face within the immersion liquid.

It is another objective of the present invention to provide the face soaking device that may be used to reduce severity of microorganism infection, including, but not limited to viral, bacterial, and/or fungal infections, of facial skin by immersing the face within the immersion liquid.

It is another objective of the present invention to provide the face soaking device that may be used to reduce severity of physical damage to facial skin by immersing the face within the immersion liquid.

It is another objective of the present invention to provide the face soaking device that may permit a user to submerge the user's face within the immersion liquid by the face soaking device comprising a vessel which may be configured to hold the immersion liquid.

It is another objective of the present invention to provide the face soaking device that may permit the user to breath while the user's face may be immersed in the immersion liquid.

It is another objective of the present invention to provide the face soaking device that may permit the user to immerse the user's face within the immersion liquid while maintaining comfort to the neck where the neck may contact the face soaking device, particularly where the soft tissue of the neck may contact the face soaking device.

It is another objective of the present invention to provide the face soaking device that may minimize immersion liquid spillage around the user's neck when the user's face may be immersed within the immersion liquid.

It is another objective of the present invention to provide the face soaking device that may catch spilled immersion liquid from a main vessel (e.g., the vessel) holding the immersion liquid.

It is another objective of the present invention to provide the face soaking device that may permit the user to immerse the user's face within the immersion liquid while maintaining comfort to the neck and mitigating against neck strain, by supporting a portion of the user's head that may be within the vessel, particularly that of the forehead.

It is another objective of the present invention to provide the face soaking device, wherein a head support (e.g., a head rest subassembly) may be adjustable; wherein such adjustments may be in a vertical direction (height direction) and/or in a forwards-backwards direction.

It is another objective of the present invention to provide the face soaking device wherein the immersion liquid may receive various gasses into the immersion liquid.

It is another objective of the present invention to provide the face soaking device wherein the immersion liquid may be oxygenated by a release of air and/or oxygen within the immersion liquid.

It is another objective of the present invention to provide the face soaking device wherein a temperature of the immersion liquid may be increased or decreased with respect to a room temperature of the face soaking device.

It is another objective of the present invention to provide the face soaking device wherein the vessel may be insulated to help control the temperature of the immersion liquid.

It is another objective of the present invention to provide the face soaking device wherein the face soaking device may be used for heat therapy and/or for cold therapy.

It is another objective of the present invention to provide the face soaking device wherein the face soaking device may be used for heat therapy and/or for cold therapy, wherein the heat therapy and/or the cold therapy may be used to treat not only skin problems, but also other ailments, such as, but not limited to, arthritis, osteoarthritis, fibromyalgia, joint stiffness, bursitis, tendonitis, sprains, pulled muscles, and the like.

It is another objective of the present invention to provide the face soaking device wherein the face soaking device may be used for heat therapy and/or for cold therapy, wherein the heat therapy and/or the cold therapy may increase blood flow, improve joint stiffness, reduce pain, and the like.

It is another objective of the present invention to provide the face soaking device wherein the face soaking device may be used for cold therapy, wherein the cold therapy may increase blood flow, improve joint stiffness, reduce pain, reduce swelling, and the like.

It is another objective of the present invention to provide the face soaking device wherein the face soaking device may be used for alternating between heat therapy and cold therapy, wherein the alternating heat and cold therapy may increase blood flow, improve joint stiffness, reduce pain, reduce swelling, improve healing, aid in removing cellular toxins, and the like.

It is another objective of the present invention to provide the face soaking device wherein the face soaking device may be used for soaking facial skin for at least a purpose of softening such facial skin and/or for softening facial hair (e.g., whiskers and/or stubble). For example, such skin softening may be beneficial for facial shaving.

It is another objective of the present invention to provide the face soaking device wherein the face soaking device may be used for treating burns, external and/or internal.

It is another objective of the present invention to provide the face soaking device wherein the face soaking device may be used for lightening skin shading.

It is another objective of the present invention to provide the face soaking device wherein the face soaking device may be used for darkening skin shading (e.g., skin tone or skin hue).

It is another objective of the present invention to provide the face soaking device wherein the immersion liquid may be paraffin wax.

It is another objective of the present invention to provide the face soaking device wherein interior surface of the vessel may be smooth to facilitate draining of the immersion liquid and to facilitate cleaning and sanitation of the face soaking device.

It is another objective of the present invention to provide the face soaking device that may be portable and that may be carried by a single adult user.

It is another objective of the present invention to provide the face soaking device wherein interior surfaces of the vessel may comprise one or more jet nozzles, one or more intakes, and a means for pumping the immersion liquid from the intakes and through the jet nozzles such that a pressure of immersion liquid may be directed to portions of the immersed face.

It is another objective of the present invention to provide the face soaking device wherein jet nozzle positioning may be adjustable.

It is another objective of the present invention to provide the face soaking device wherein facial immersion within the immersion liquid within the vessel may be soothing and relaxing to the user, such stress may be reduced.

It is another objective of the present invention that such a stress releasing use of the face soaking device may result in further collateral benefits such as promoting lowering of blood pressure, mitigation against headache severity, and/or strengthening the user's immune system.

It is yet another objective of the present invention to provide a face soaking device that may utilize, quality and reliable manufacturing methods, but that may also be efficient and less expensive manufacturing methods.

These and other advantages and features of the present invention are described herein with specificity so as to make the present invention understandable to one of ordinary skill in the art, both with respect to how to practice the present invention and how to make the present invention.

BRIEF DESCRIPTION OF THE SEVERAL VIEWS OF THE DRAWINGS

Elements in the figures have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention.

FIG. 2B also includes sectional-line 7-7.

FIG. 2D may depict a back view of a front portion of the face soaking device of FIG. 2A.

FIG. 4C may depict a top view of a front portion of the face soaking device of FIG. 4A.

FIG. 6C may depict the clamp of FIG. 6A, shown from a back view.

Figure 1:
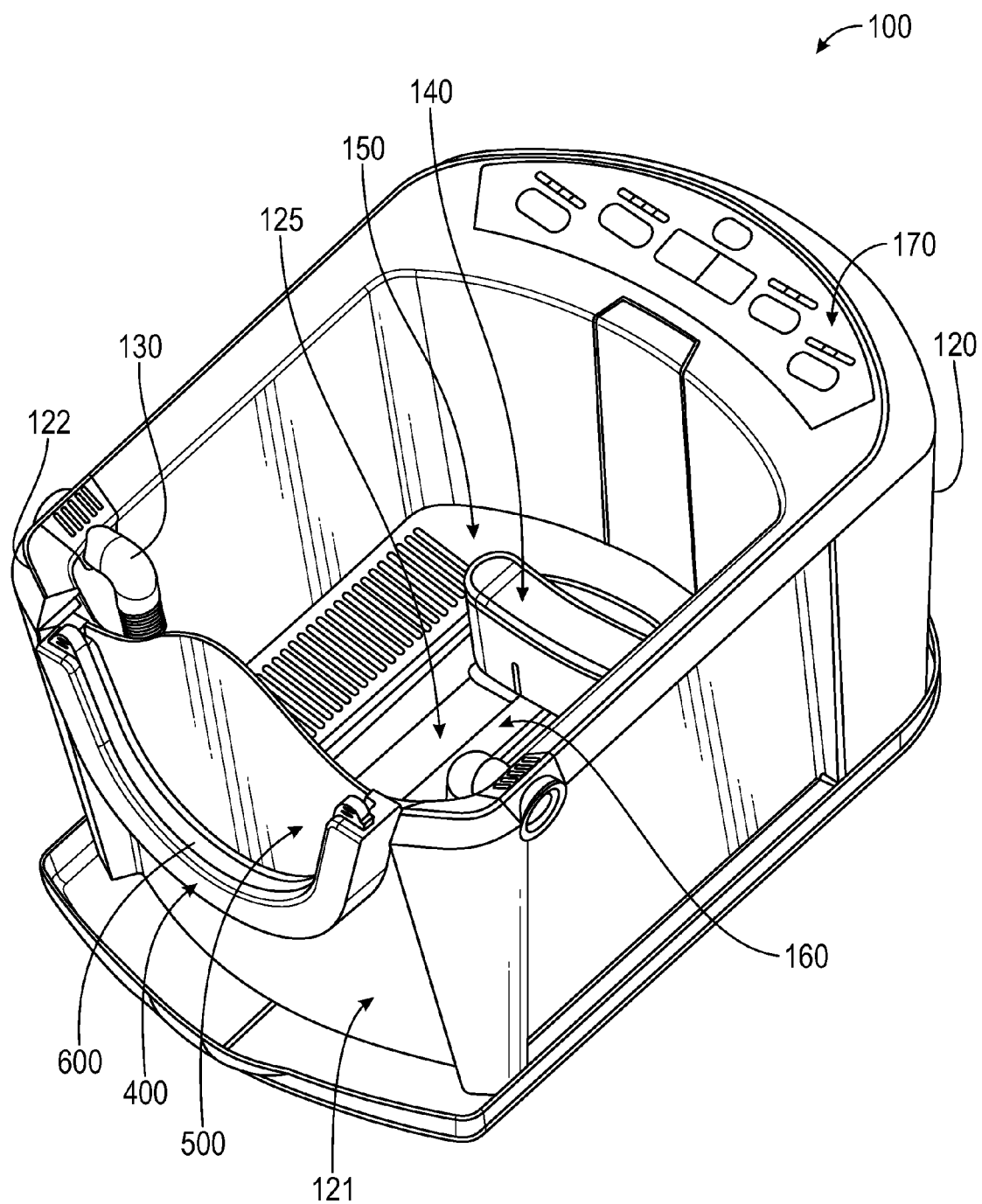
FIG. 1 may depict an embodiment of an overall assembled face soaking device, shown from a top perspective view.

REFERENCE NUMERAL SCHEDULE 100 face soaking device 100
120 vessel 120
121 at least one wall 121
122 rim 122
125 at least one base 125
130 breathing apparatus 130
140 head rest subassembly 140
150 heater subassembly 150
160 aerator 160
170 controls 170
400 neck-gasket-accommodator 400
402 contour 402
404 horizontal width 404
406 maximum vertical length 406
408 receiving-channel 408
410 two opposing opening wall-edges 410
412 pocket 412
500 vessel neck gasket 500
501 mating edge 501
503 top edge 503
505 flexible member 505
507 internal surface 507
509 external surface 509
511 carrier 511
600 clamp 600
601 terminal end 601
603 mating-wall-edge 603
605 snap latch 605
800 clamp 800
811 finger-pull 811
813 chamfer 813
815 tab 815
900 clamp 900
911 finger-pull 911
1000 clamp 1000
1011 finger-pull 1011
1100 clamp 1100

DETAILED DESCRIPTION OF THE INVENTION

In the following discussion that addresses a number of embodiments and applications of the present invention, reference is made to the accompanying drawings that form a part thereof, where depictions are made, by way of illustration, of specific embodiments in which the invention may be practiced. It is to be understood that other embodiments may be utilized and changes may be made without departing from the scope of the invention.

FIG. 1 may depict an embodiment of an overall assembled face soaking device 100, shown from a top perspective view. In some exemplary embodiments, as may be depicted in FIG. 1, face soaking device 100 may comprise: a vessel 120, a vessel neck gasket 500, and a breathing apparatus 130.

Continuing discussing FIG. 1, in some embodiments, vessel 120 may be hold a liquid in a sufficient volume to submerge a whole face of a user or a portion thereof. It is obvious to one of ordinary skill in the art, that vessel 120 may be configured to hold the liquid at a sufficient level to permit the user to submerge (immerse) the whole of their face, or a portion thereof within the liquid, while the liquid may be held within vessel 120. This sufficient level may be a liquid level where when the user inserts their face into an internal volume of vessel 120 and rests a first portion of their neck upon a vessel neck gasket 500, such that their face may be completely immersed in the liquid. The maximum liquid level of vessel 120 may be greater (higher) than this sufficient level.

In some embodiments, vessel 120 may comprise at least one wall 121 and at least one base 125. At least one wall 121 and at least one base 125 may be in physical contact with each other. At least one wall 121 may comprise a neck-gasket-accommodator 400. (See e.g., FIG. 4A for neck-gasket-accommodator 400.) Neck-gasket-accommodator 400 may be configured to accommodate vessel neck gasket 500. In some embodiments, neck-gasket-accommodator 400 may be formed as a cutout into a region of at least one wall 121, from a top of vessel 120. In some embodiments, neck-gasket-accommodator 400 may be formed as an integral molded structure of a region of at least one wall 121. Vessel neck gasket 500 may be removably joined to vessel 120. Where vessel neck gasket 500 may join vessel 120, i.e., along such surfaces of physical contact, a primary water tight seal may be formed in or at the vicinity of neck-gasket-accommodator 400. For example, and without limiting the scope of the present invention, in some embodiments, this "vicinity" of neck-gasket-accommodator 400 may be two inches or less from structure of neck-gasket-accommodator 400. In other embodiments, other distances may be used for the "vicinity" of neck-gasket-accommodator 400. Vessel neck gasket 500 may receive a first portion of a neck region of the user when the whole face or the first portion thereof may be submerged in the liquid within the internal volume of vessel 120. The first portion of the neck region of the user may be where their neck physically contacts vessel neck gasket 500. Note, the nature of the physical contact between the first portion of the neck region of the user and vessel neck gasket 500 may be removable. When vessel neck gasket 500 may receive the first portion of the neck region of the user, a secondary water tight seal may be formed between this first portion of the neck region and vessel neck gasket 500.

In some embodiments, vessel 120 may be double hulled.

In some embodiments, breathing apparatus 130 may be in physical contact with vessel 120, as may be shown in FIG. 1. In some embodiments, a breathing apparatus embodiment may be in physical contact with a head rest subassembly. In both such embodiments, the nature of the physical contact between breathing apparatus embodiments (e.g., 130) and vessel 120; or between breathing embodiments and the given head rest subassembly, may be removable in some embodiments; while non-removable in other embodiments. In some embodiments, the user may be able to breathe using breathing apparatus 130 when a mouth of the user may be holding a mouth piece of breathing apparatus 130.

When vessel 120 may be filled with the liquid to a level at or less than a maximum liquid level of vessel 120, the user may soak their whole face or the portion thereof for a time period. The skin being soaked in the liquid for this time period may receive a health, an aesthetic, and/or a soothing benefit.

In some embodiments, the benefit may comprise one or more of a reduction in acne, a reduction in wrinkle severity, a softening of skin, moisturizing of skin, promotion of relaxation, promotion of healing of damaged skin, promotion of healing of infected skin, reduction in rash severity, reduction and/or elimination of headaches (including migraine), promotion of healing of traumatized tissue (including burned tissue), lightening skin shades, darkening skin shades (tone, hue), reduction in swelling, and the like. Such benefits may derive from facial skin exposure to the liquid where characteristics of the liquid may comprise one or more of the liquid being a saline solution, the liquid being a saline solution with a salt concentration greater than 0.9% by weight, presence of air and/or oxygen within the liquid, temperature of the liquid being less than or greater than ambient room temperature, circulation of the liquid within vessel 120, and/or the liquid being directed against a portion of the skin in the form of stream or jet of the liquid pressure.

In some embodiments, face soaking device 100 may further comprise a head rest subassembly 140. In some embodiments, at least some portion of head rest subassembly 140 may be attached to vessel 120. See e.g., FIG. 1. In some embodiments, the at least some portion of head rest subassembly 140 may be removably attached to vessel 120. In some embodiments, head rest subassembly 140 may comprise a support member or a strap. In some embodiments, at least some portion of the support member or at least some portion of the strap may be located in the internal volume of vessel 120. In some embodiments, the support member or the strap physically supports a portion of the head (e.g., a forehead) of the user when the whole face or portion thereof is removably located in the internal volume of vessel 120. See e.g., FIG. 1.

In some embodiments, face soaking device 100 may further comprise a heater subassembly 150. In some embodiments, at least a portion of heater subassembly 150 may be attached to vessel 120. See e.g., FIG. 1. In some embodiments, heater subassembly 150 may comprise a heating element that heats at least a portion of the liquid within the internal volume of vessel 120. In some embodiments, heater subassembly 150 may provide heating and/or cooling to the at least the portion of the liquid within the internal volume of vessel 120.

In some embodiments, face soaking device 100 may further comprise an aerator 160. See e.g., FIG. 1. In some embodiments, aerator 160 may comprise a gas diffuser and a gas source in physical communication with the gas diffuser. In some embodiments, the gas diffuser may be attached to vessel 120. In some embodiments, the gas diffuser may be removably attached to vessel 120. In some embodiments, the gas source provides gas to the gas diffuser. In some embodiments, the gas diffuser releases at least some of the gas received through a porous structure of the gas diffuser into the internal volume of vessel 120; such that bubbles may be released into at least some of the liquid in the internal volume of vessel 120.

In some embodiments, face soaking device 100 may further comprise at least one electromagnetic (EM) emitter. In some embodiments, the at least one EM emitter emits electromagnetic radiation at predetermined wavelengths. In some embodiments, at least some portion of the at least one EM emitter may be attached to vessel 120. In some embodiments, at least some of emitted electromagnetic radiation is emitted into the internal volume of vessel 120. For example, and without limiting the scope of the present invention, in some embodiments, the at least one EM emitter may comprise at least one light source, such as, but limited to a LED (light emitting diode) or one or more banks of LEDs.

In some embodiments, face soaking device 100 may further comprise controls 170 for controlling electronics and/or electro-mechanical components of face soaking device 100. Such electronic and electro-mechanical components may comprise one or more: heater subassembly 150, aerator 160, and/or the at least one electromagnetic emitter. See e.g., FIG. 1.

Figure 2A:
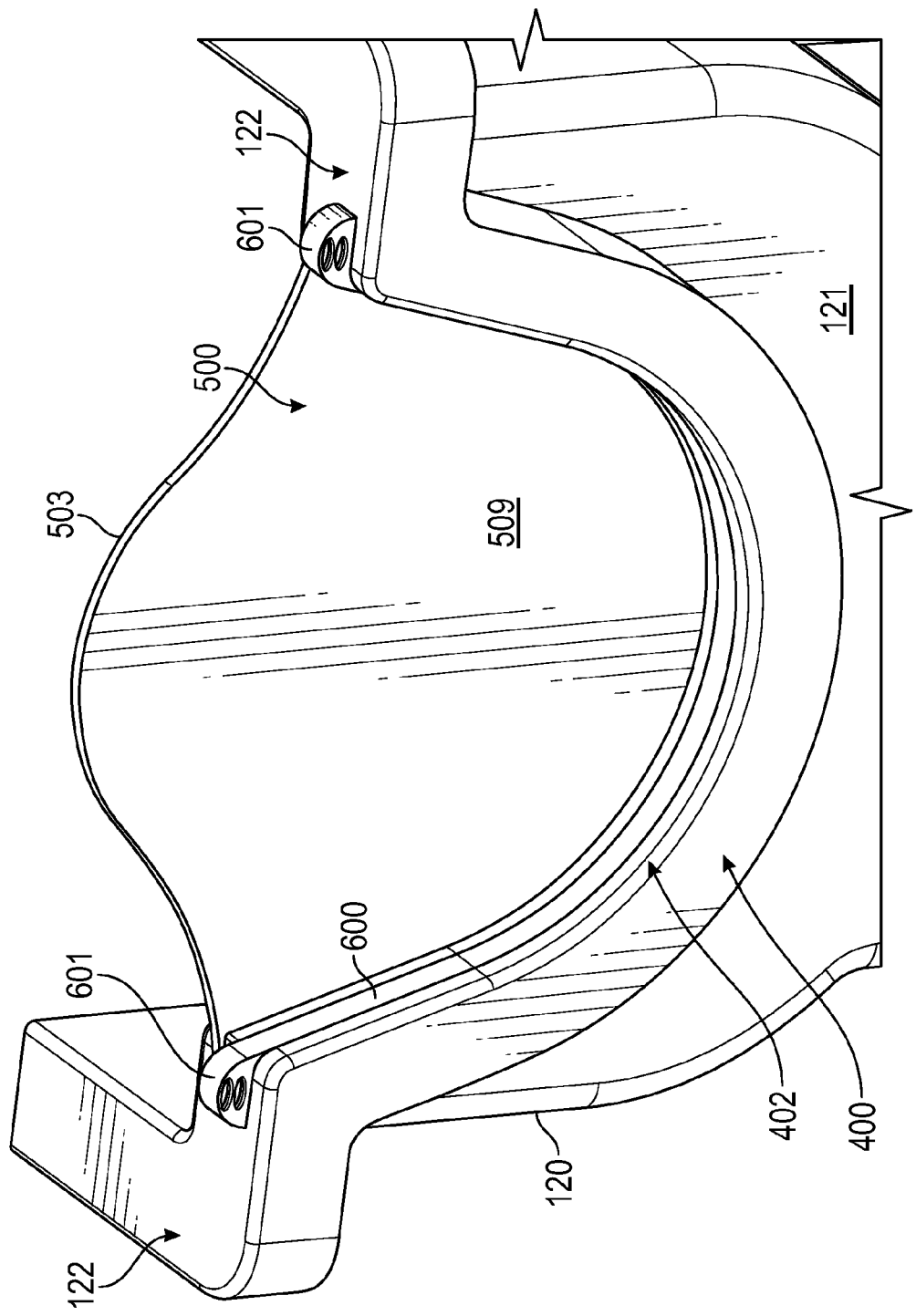
FIG. 2A may depict a close up of a front and a top portion of the face soaking device of FIG. 1.
Figure 2B:
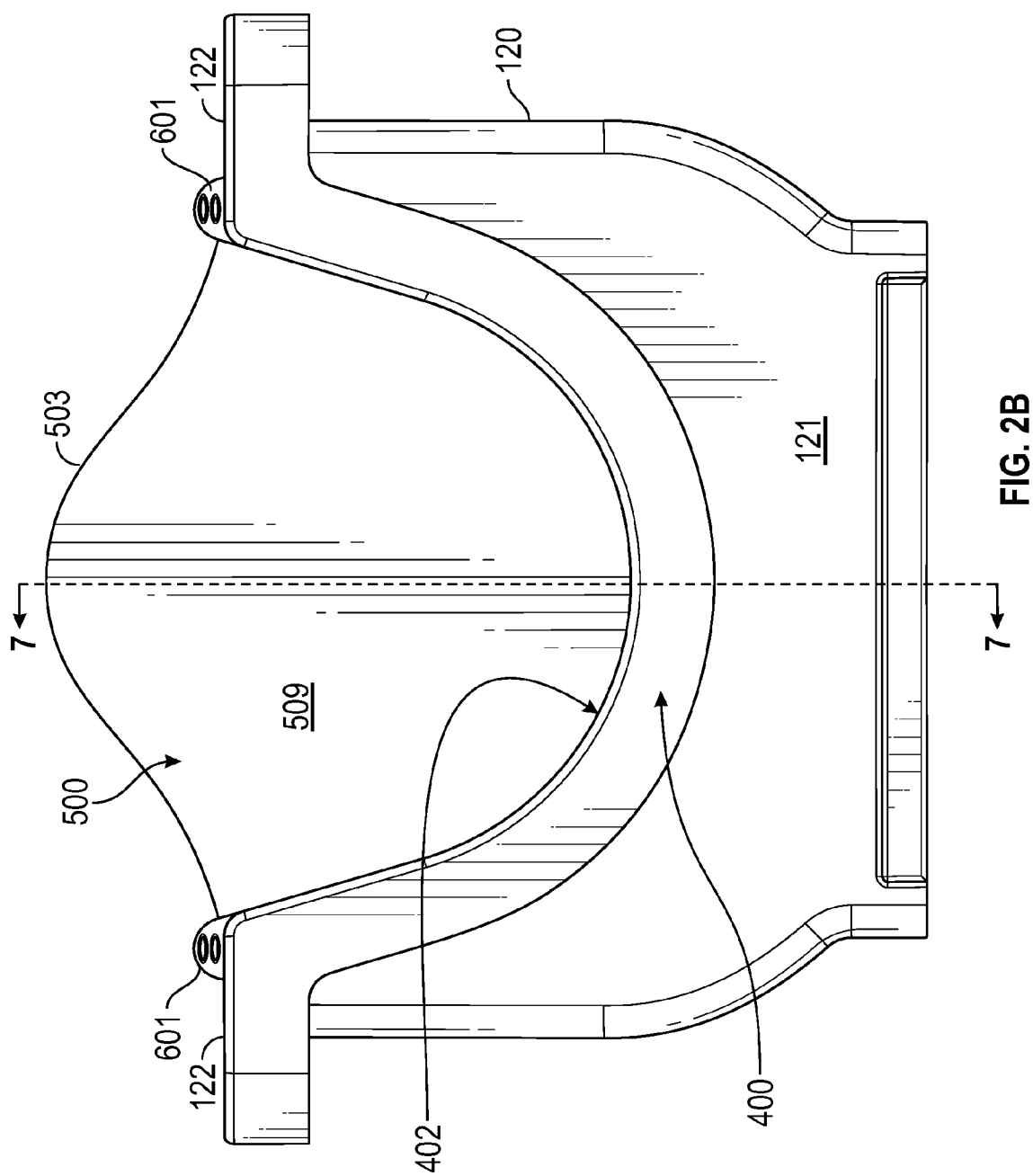
FIG. 2B may depict a front view of the face soaking device of FIG. 2A.
Figure 2C:
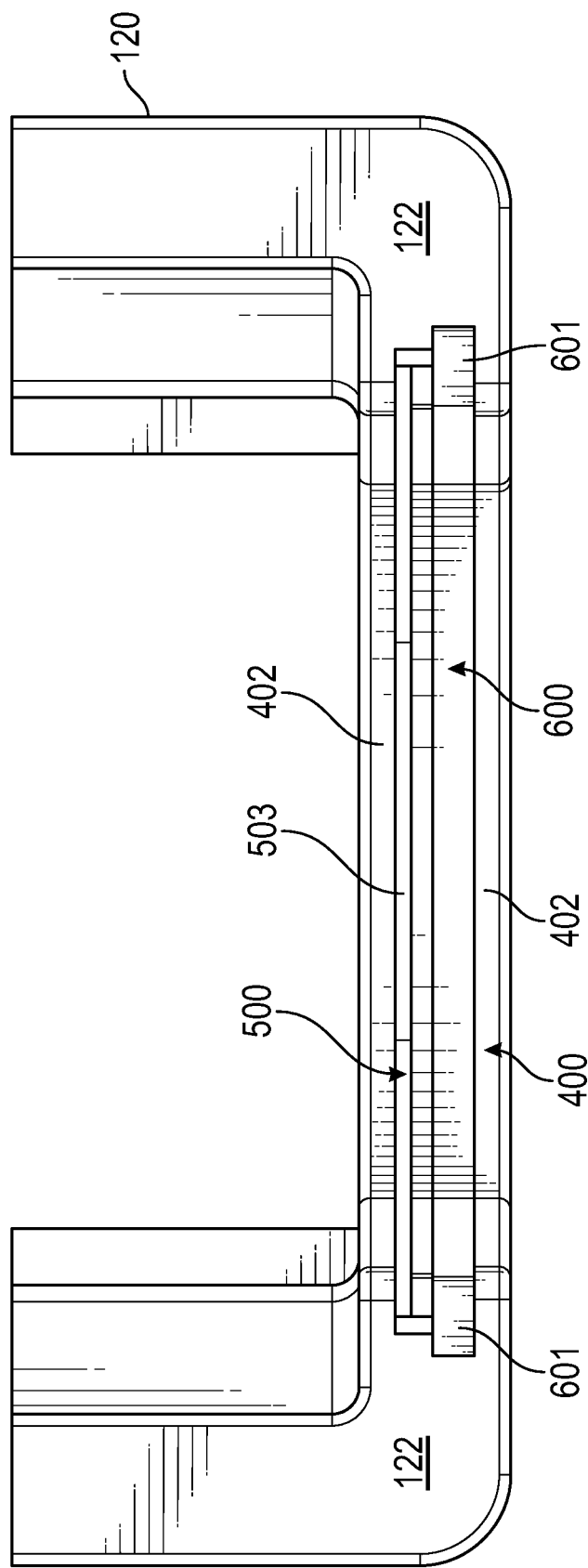
FIG. 2C may depict a top view of a front portion of the face soaking device of FIG. 2A.

A FIG. 2 series of figures may comprise FIG. 2A through FIG. 2D. These FIG. 2 series figures may depict vessel neck gasket 500 removably attached to vessel 120. In contrast, a FIG. 3 series of figures (FIG. 3A and FIG. 3B) may show vessel neck gasket 500 exploded away from vessel 120, i.e., vessel neck gasket 500 removably detached from vessel 120; a FIG. 4 series may focus on showing neck-gasket-accommodator 400 of vessel 120, i.e., where vessel neck gasket 500 removably attaches to vessel 120; a FIG. 5 series of figures may focus on showing just vessel neck gasket 500; a FIG. 6 series may focus on showing just a clamp 600, which in some embodiments, may help to removably secure vessel neck gasket 500 to neck-gasket-accommodator 400; FIG. 7 may show a cross-sectional view of the configuration where vessel neck gasket 500 is removably attached to neck-gasket-accommodator 400.

Turning back to the FIG. 2 series of figures, FIG. 2A may depict a close up of a front and a top portion of face soaking device 100 showing vessel neck gasket 500 removably attached to vessel 120. FIG. 2B may depict a front view of face soaking device 100 of FIG. 2A. FIG. 2C may depict a top view of a front portion of face soaking device 100 of FIG. 2A. FIG. 2D may depict a back view of a front portion of face soaking device 100 of FIG. 2A.

Notes: front views may also be known as a vessel neck gasket view, at least when vessel neck gasket 500 may be attached to vessel 120; a left side view may be with respect to an observer looking upon the front view, wherein the left side view may be with respect to the observer's left, i.e., the left side of face soaking device 100 (or component thereof) when viewed from the front view.

Figure 3A:
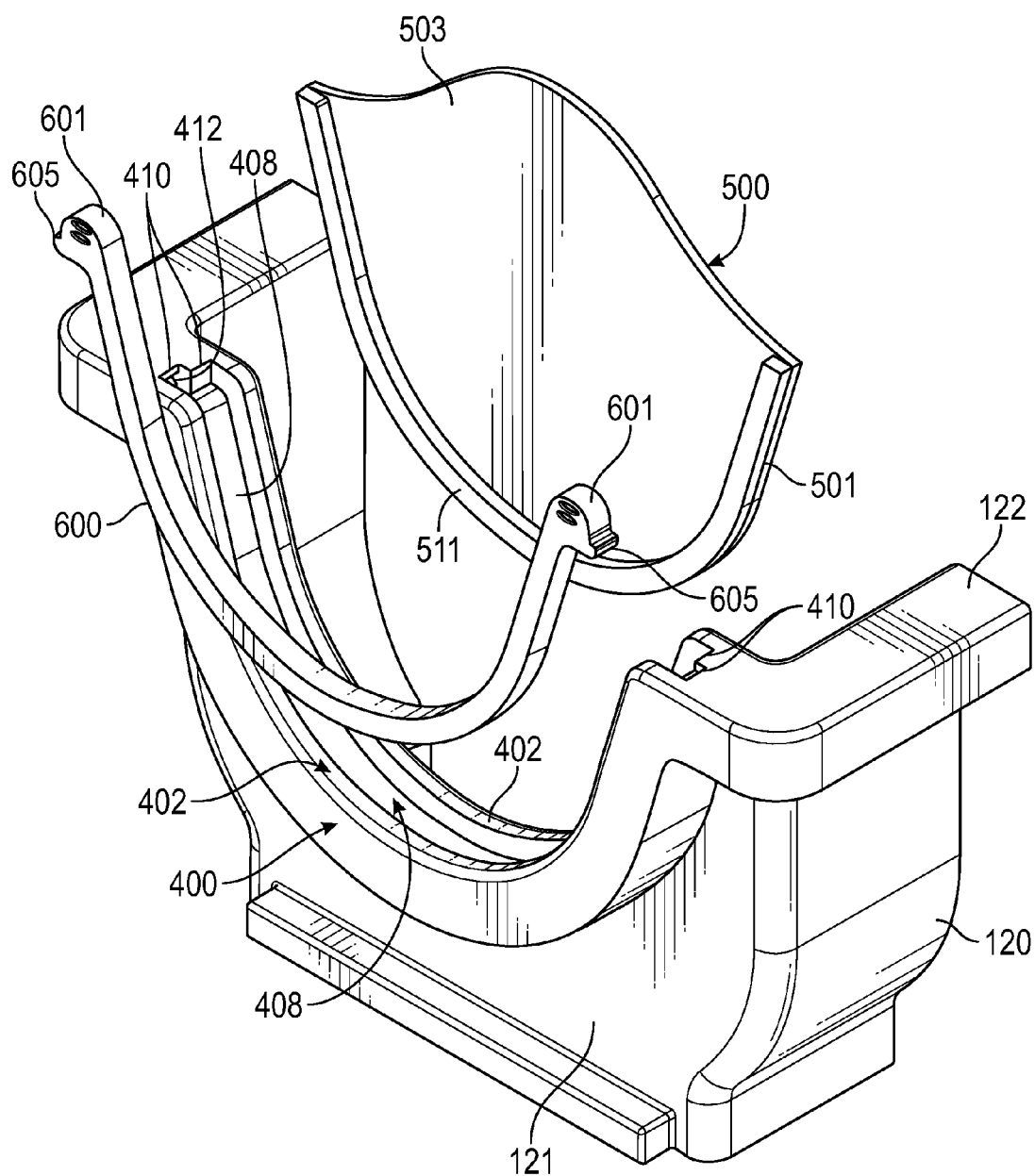
FIG. 3A may depict a partial exploded view of a front portion of the face soaking device of FIG. 2A, shown from a top front perspective view.
Figure 3B:
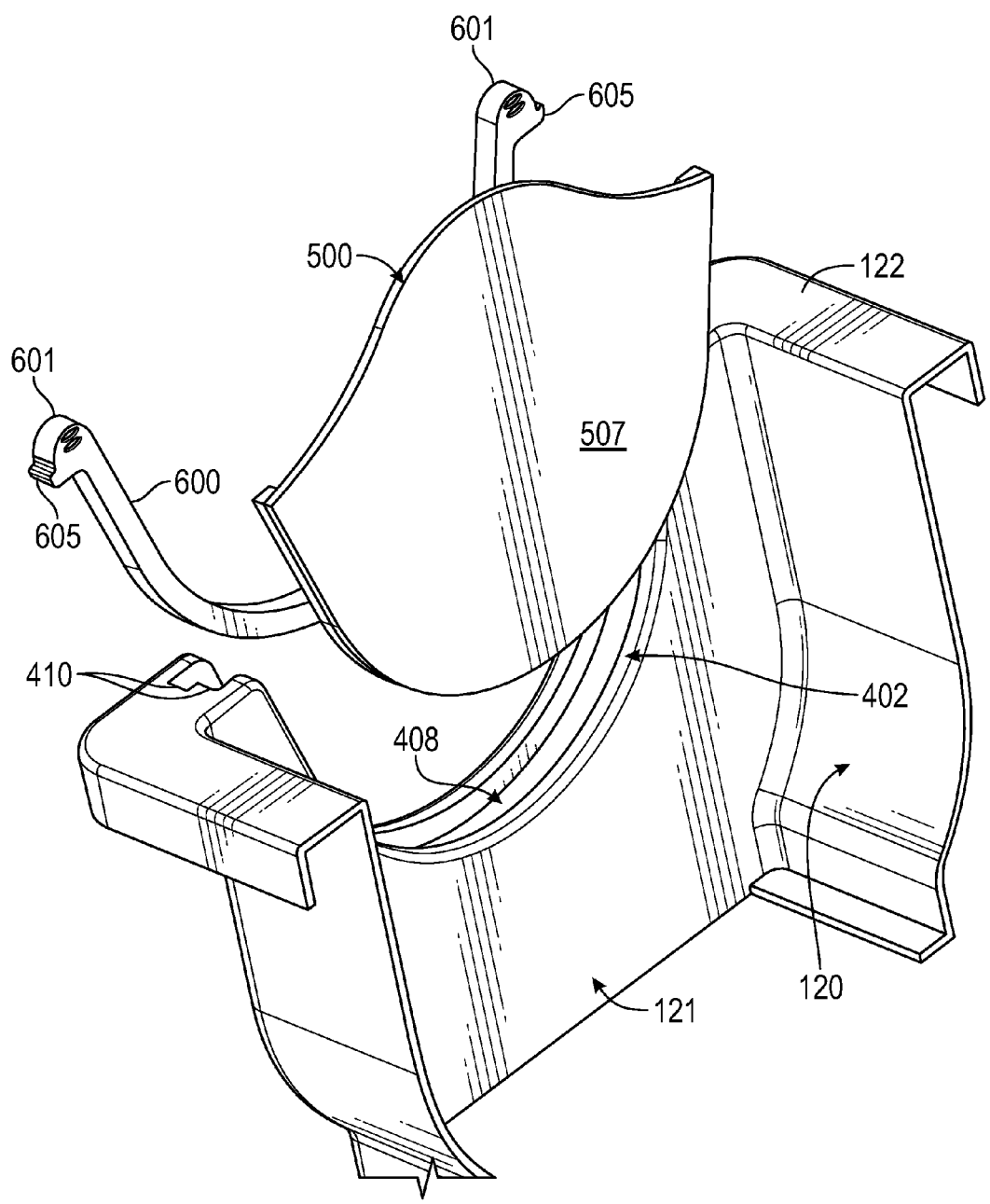
FIG. 3B may depict a partial exploded view of a front portion of the face soaking device of FIG. 2A, shown from a top back perspective view.

The FIG. 3 series of figures may comprise FIG. 3A and FIG. 3B. FIG. 3A may depict a partial exploded view of a front portion of face soaking device 100 of FIG. 2A, shown from a top front perspective view. FIG. 3B may depict a partial exploded view of a front portion of face soaking device 100 of FIG. 2A, shown from a top back perspective view. In both FIG. 3A and in FIG. 3B, vessel neck gasket 500 may be shown removed away from vessel 120. In both FIG. 3A and in FIG. 3B, portions of neck-gasket-accommodator 400 may be shown as vessel neck gasket 500 may be shown removed away from vessel 120. In both FIG. 3A and in FIG. 3B, clamp 600 may also be shown removed away from vessel 120.

In some embodiments vessel neck gasket 500 may be attached to neck-gasket-accommodator 400 by use of clamp 600. See e.g., FIG. 3A, FIG. 3B, and FIG. 7.

Figure 4A:
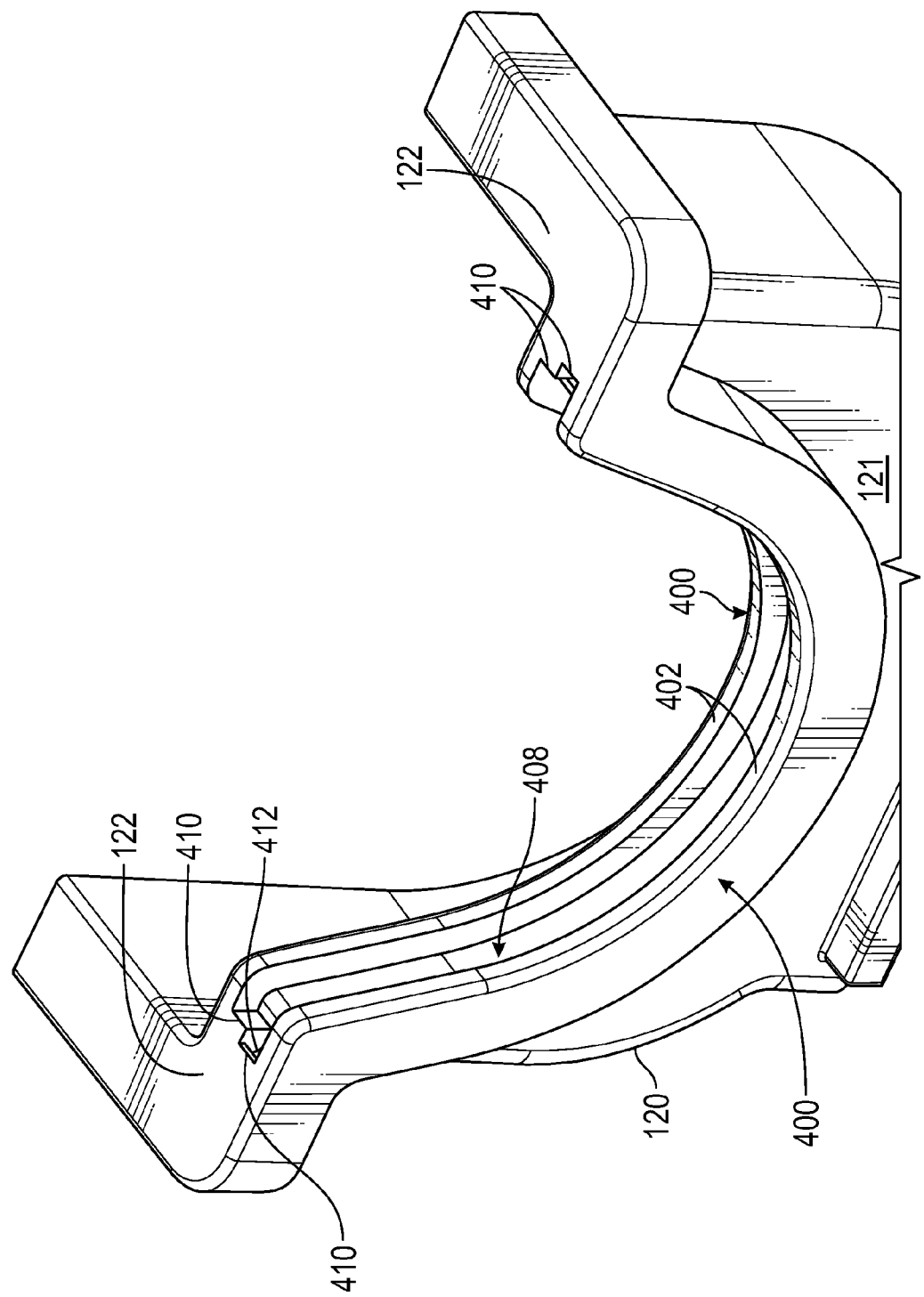
FIG. 4A may depict a close up of a front and a top portion of the face soaking device of FIG. 2A, but with a vessel neck gasket and a clamp removed, so a neck-gasket-accommodator may be visible.
Figure 4B:
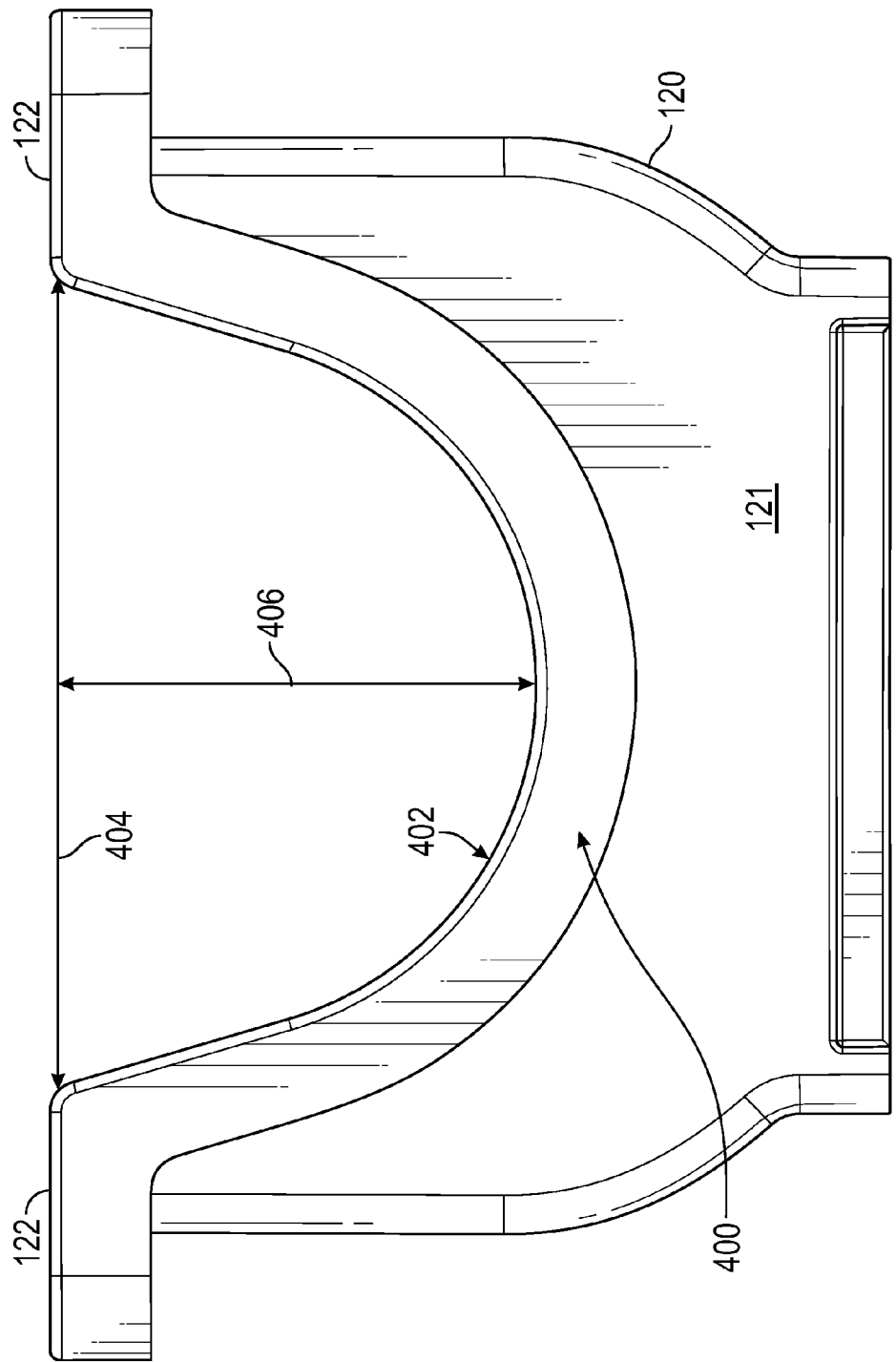
FIG. 4B may depict a front view of the face soaking device of FIG. 4A.
Figure 4D:
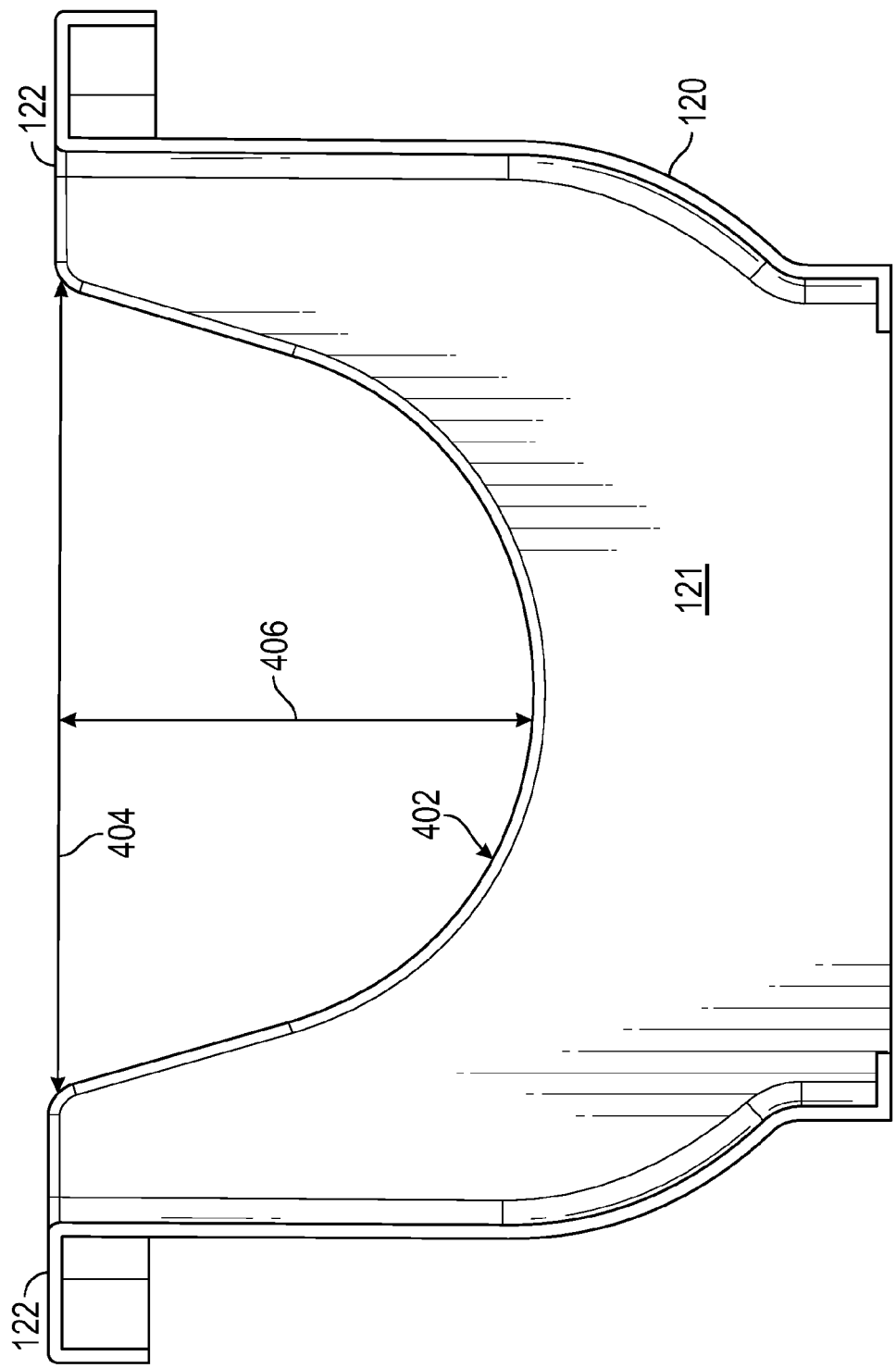
FIG. 4D may depict a back view of a front portion of the face soaking device of FIG. 4A.

The FIG. 4 series of figures may comprise FIG. 4A through FIG. 4D. As noted, these FIG. 4 series may focus on showing neck-gasket-accommodator 400 of vessel 120, i.e., where vessel neck gasket 500 removably attaches to vessel 120. Note, vessel neck gasket 500 may not be shown in the FIG. 4 series of figures. Note, vessel neck gasket 500 may not be shown in the FIG. 4 series of figures. Note, clamp 600 may not be shown in the FIG. 4 series of figures. FIG. 4A may depict a close up of a front and a top portion of face soaking device 100 of FIG. 2A. FIG. 4B may depict a front view of face soaking device 100 of FIG. 4A. FIG. 4C may depict a top view of a front portion of face soaking device 100 of FIG. 4A. FIG. 4D may depict a back view of a front portion of face soaking device 100 of FIG. 4A. FIG. 4A may correspond to FIG. 2A, FIG. 4B may correspond to FIG. 2B, FIG. 4C may correspond to FIG. 2C, and FIG. 4D may correspond to FIG. 2D; but in these FIG. 4 series of figures vessel neck gasket 500 and clamp 600 may be removed from vessel 120, so neck-gasket-accommodator 400 may be visible.

Figure 5A:
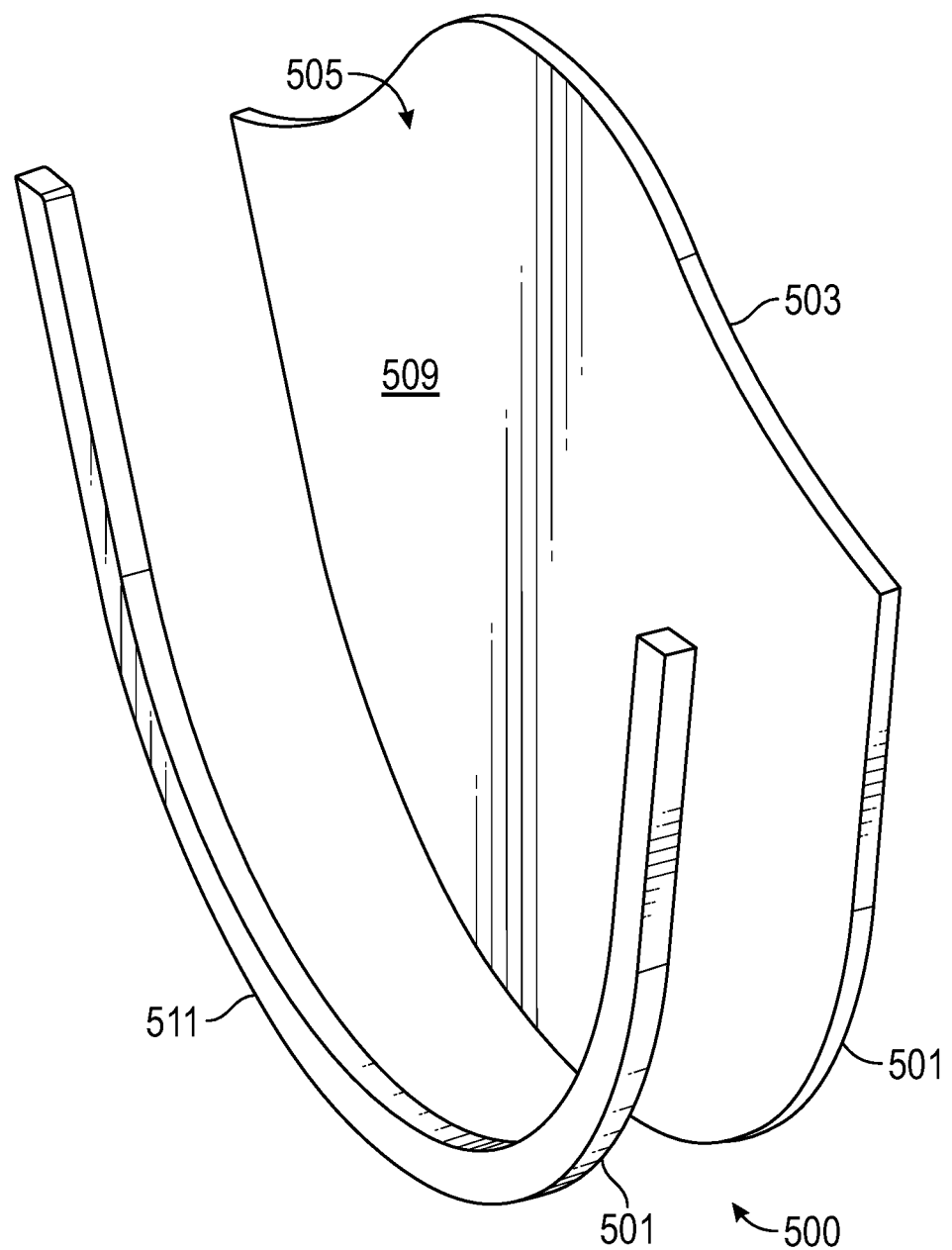
FIG. 5A may depict an exploded view of a vessel neck gasket; wherein a carrier may be separated from a flexible member, shown from a top front perspective view.
Figure 5B:
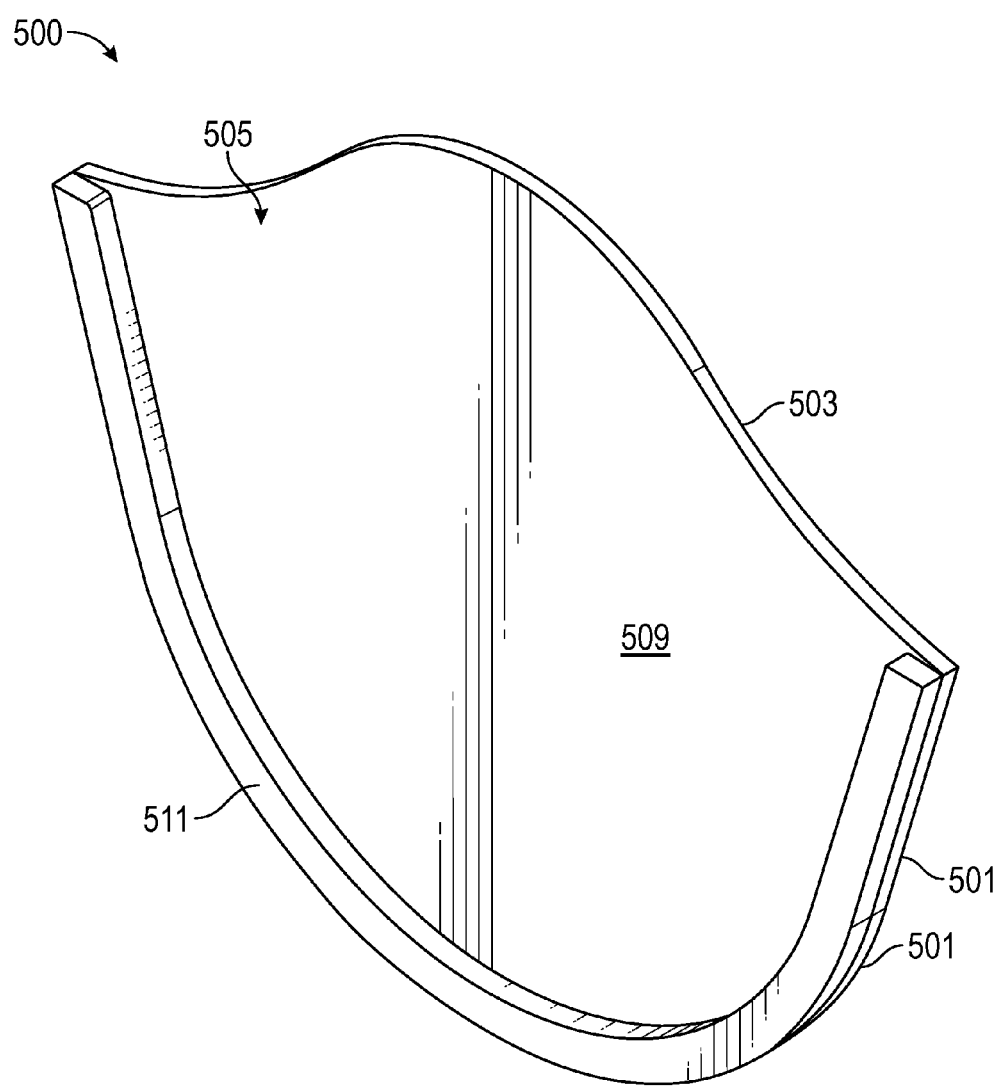
FIG. 5B may depict the assembled vessel neck gasket of FIG. 5A, shown from a top front perspective view.
Figure 5C:
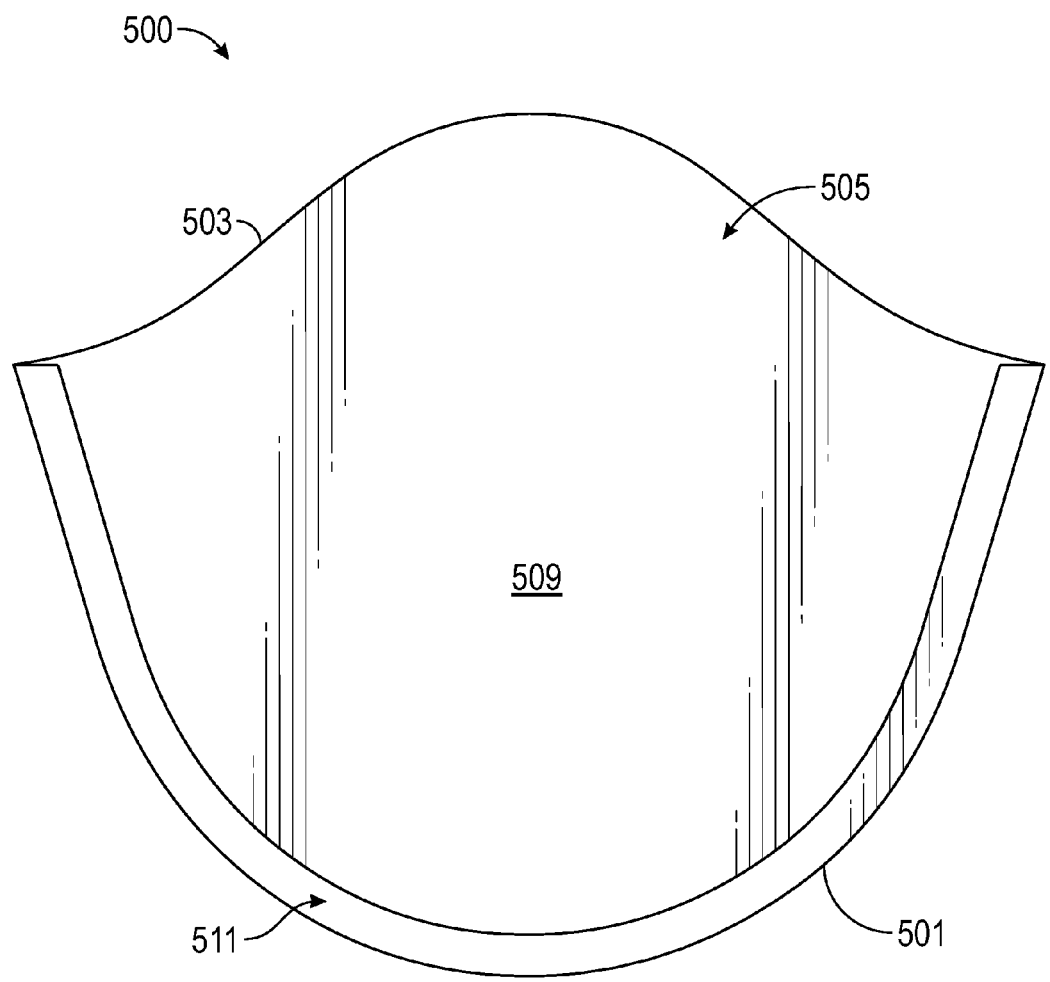
FIG. 5C may depict the assembled vessel neck gasket of FIG. 5A, shown from a front view.
Figure 5D:
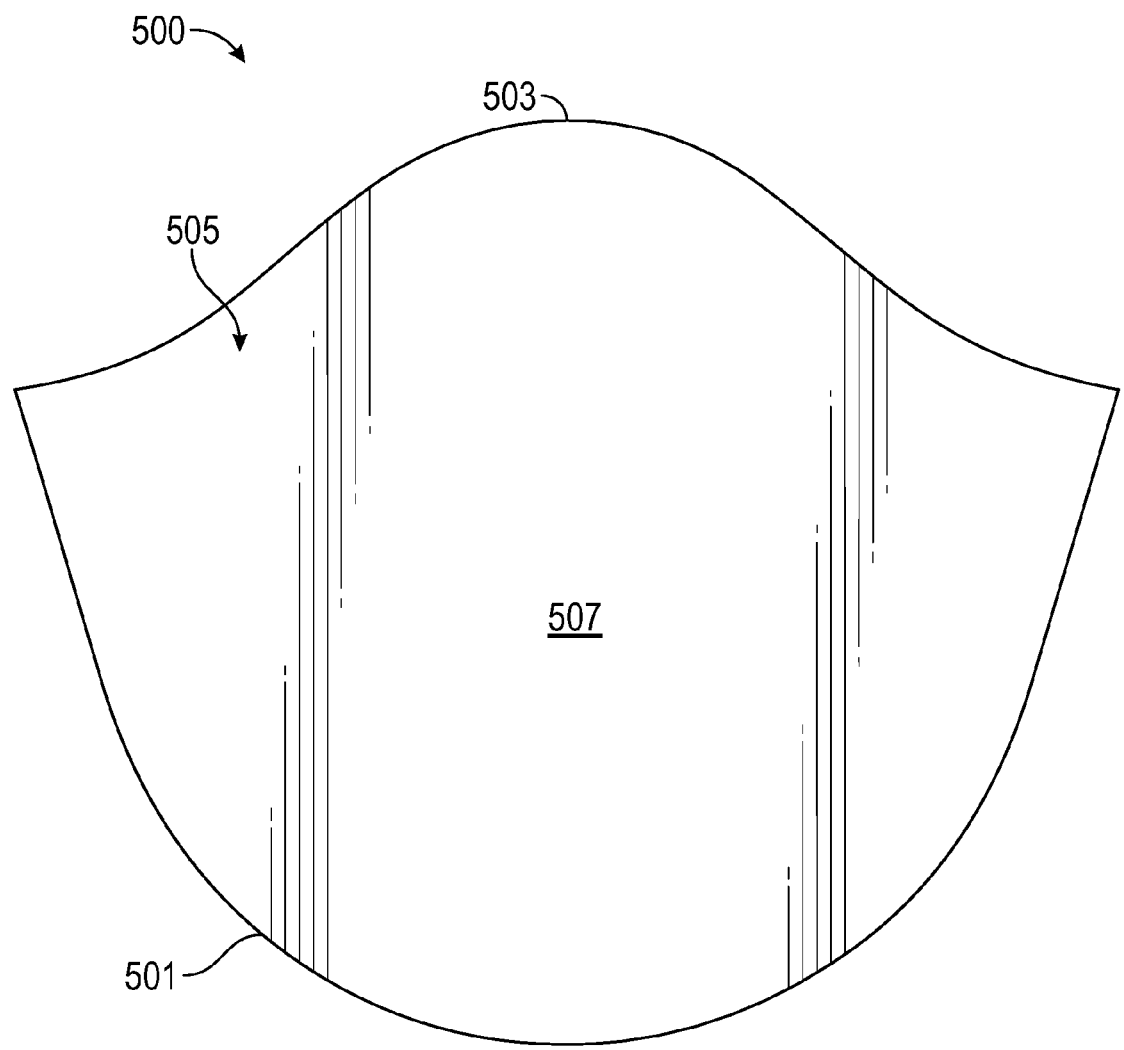
FIG. 5D may depict the assembled vessel neck gasket of FIG. 5A, shown from a back view.
Figure 5E:
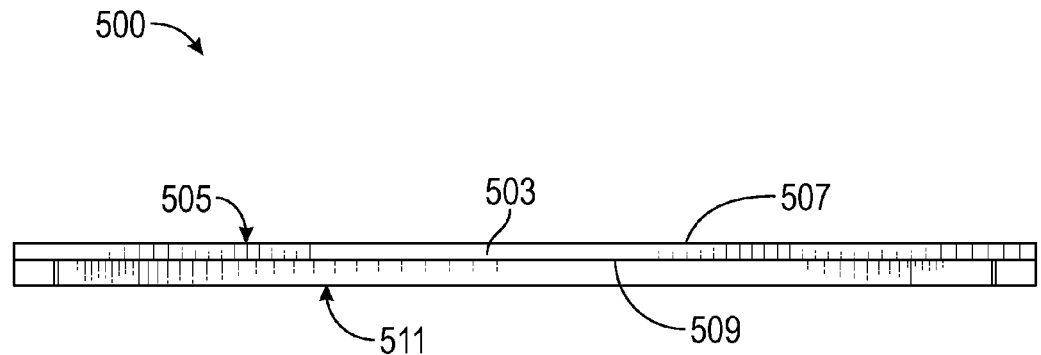
FIG. 5E may depict the assembled vessel neck gasket of FIG. 5A, shown from a top view.
Figure 5F:
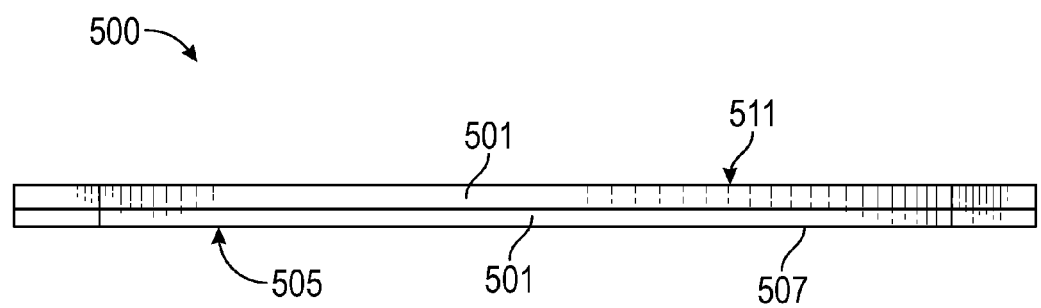
FIG. 5F may depict the assembled vessel neck gasket of FIG. 5A, shown from a bottom view.
Figure 5G:
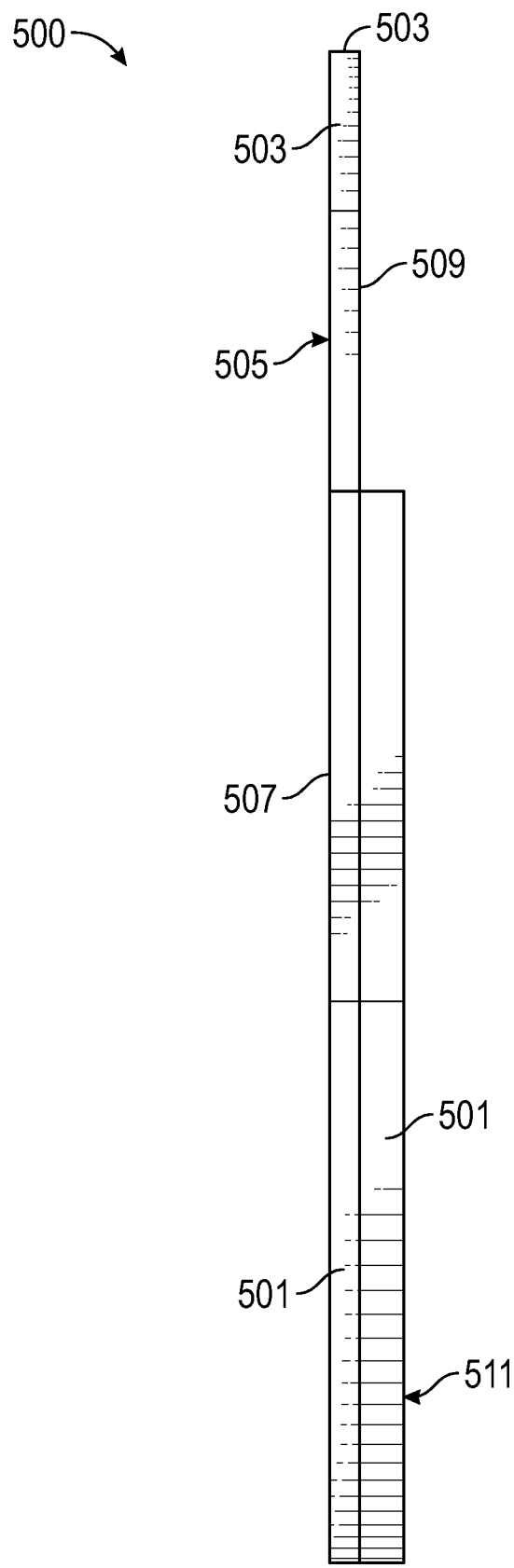
FIG. 5G may depict the assembled vessel neck gasket of FIG. 5A, shown from a left side view. (A right side view may be a minor image of FIG. 5G.)

The FIG. 5 series of figures may comprise FIG. 5A through FIG. 5G. As noted, these FIG. 5 series of figures may focus on showing just vessel neck gasket 500. FIG. 5A may depict an exploded view of vessel neck gasket 500; wherein a carrier 511 may be separated from a flexible member 505, shown from a top front perspective view. FIG. 5B may depict the assembled vessel neck gasket 500, shown from a top front perspective view. FIG. 5C may depict the assembled vessel neck gasket 500, shown from a front view. FIG. 5D may depict the assembled vessel neck gasket 500, shown from a back view. FIG. 5E may depict the assembled vessel neck gasket 500, shown from a top view. FIG. 5F may depict the assembled vessel neck gasket 500, shown from a bottom view. FIG. 5G may depict the assembled vessel neck gasket 500, shown from a left side view. (A right side view may be a mirror image of FIG. 5G.)

Figure 6A:
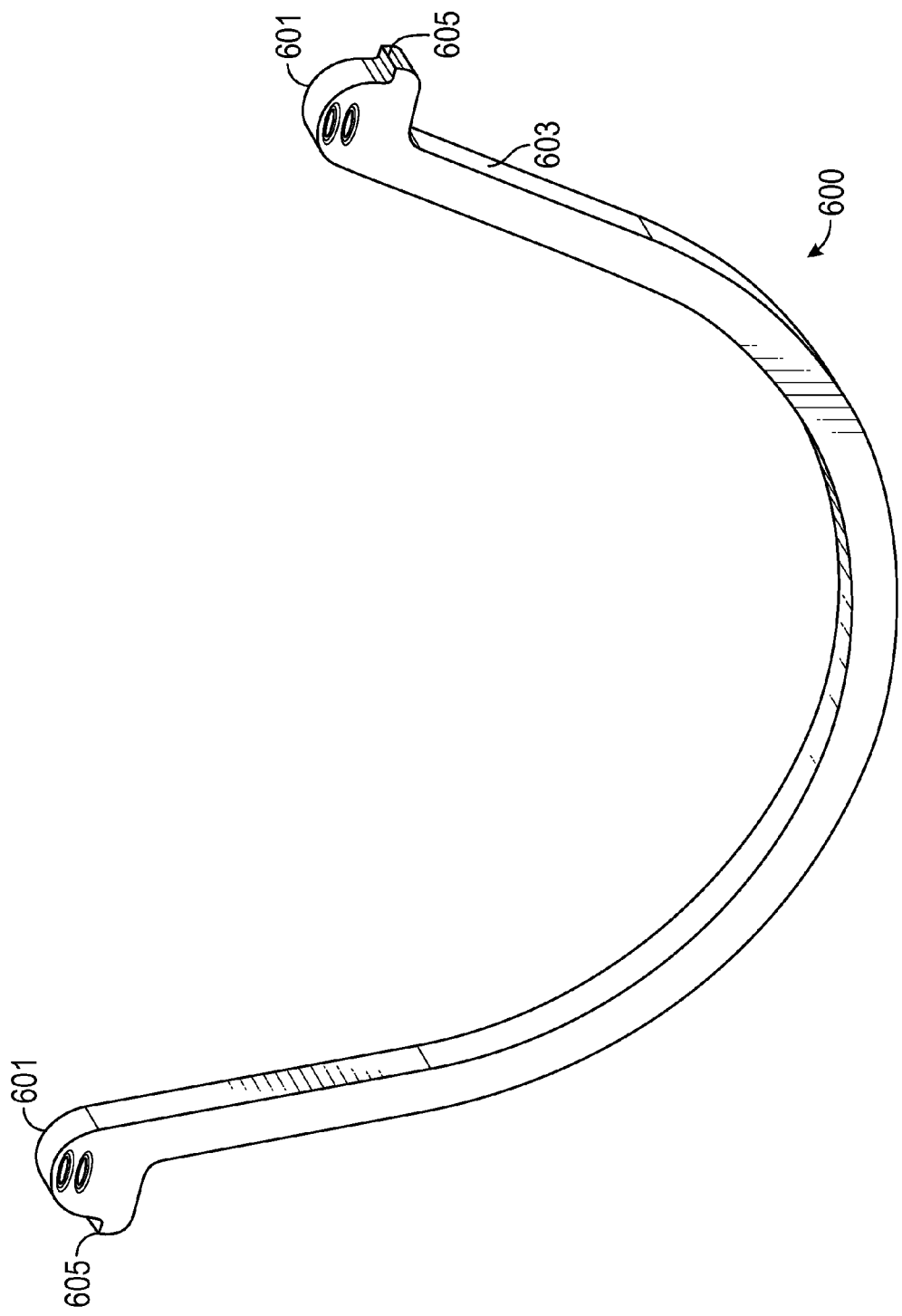
FIG. 6A may depict a clamp, shown from a top front perspective view.
Figure 6B:
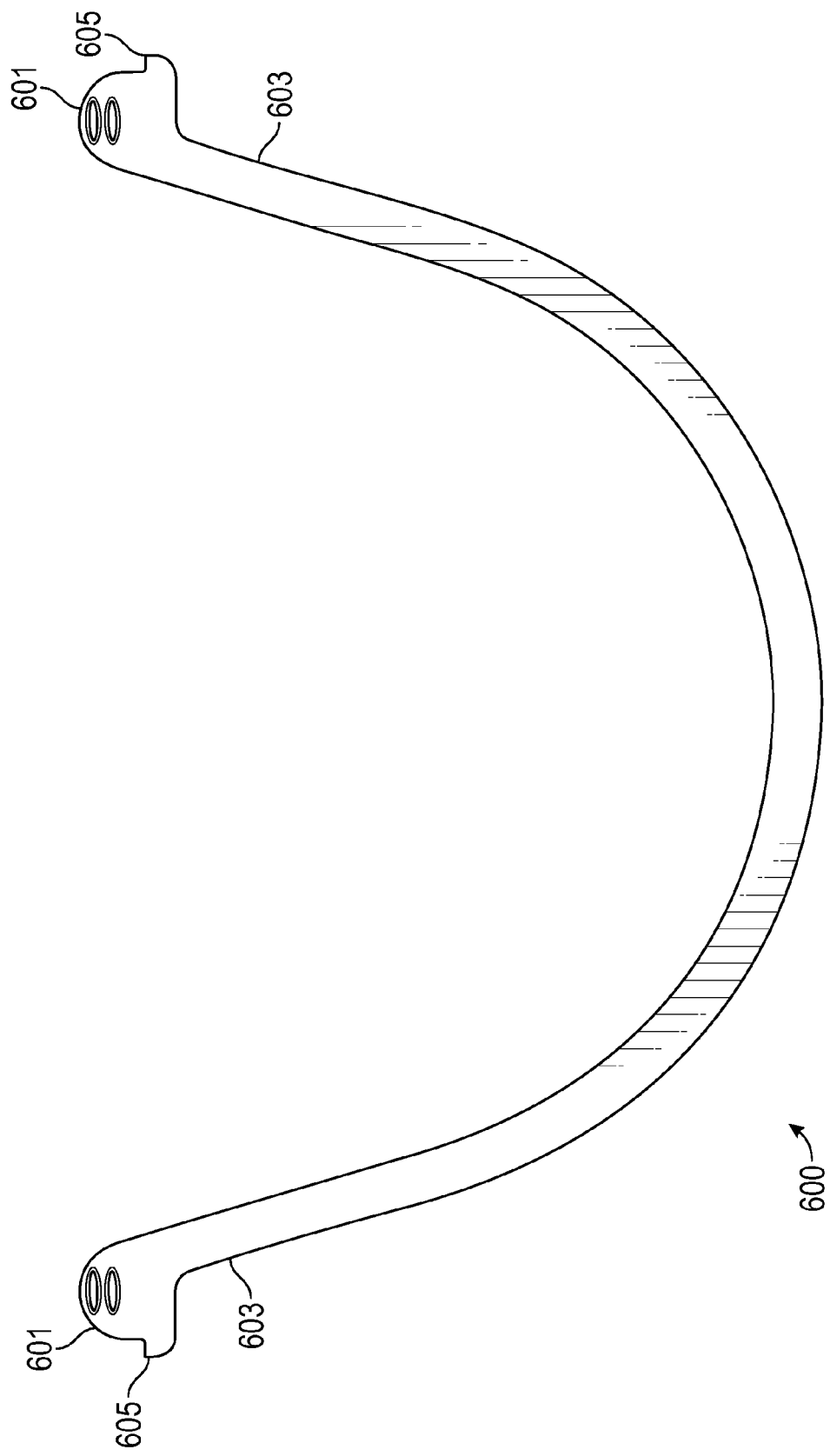
FIG. 6B may depict the clamp of FIG. 6A, shown from a front view.
Figure 6D:
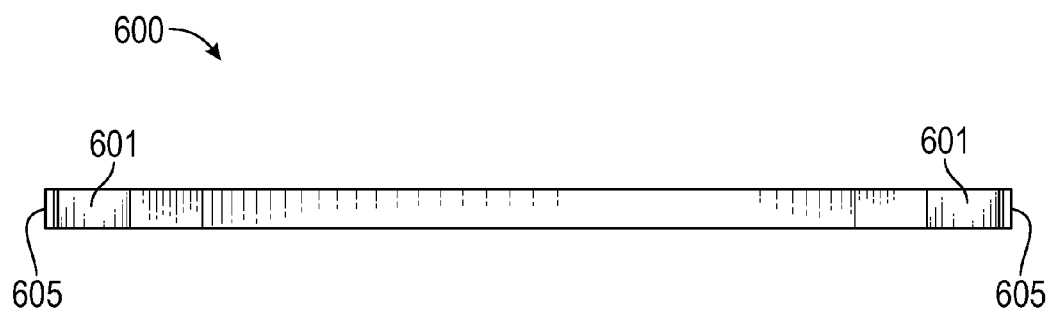
FIG. 6D may depict the clamp of FIG. 6A, shown from a top view.
Figure 6E:
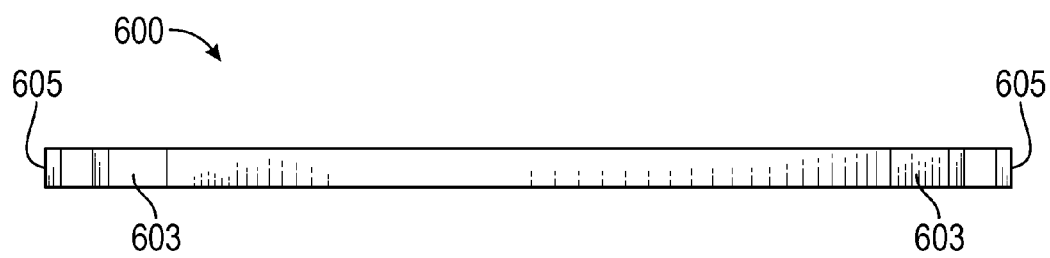
FIG. 6E may depict the clamp of FIG. 6A, shown from a bottom view.
Figure 6F:
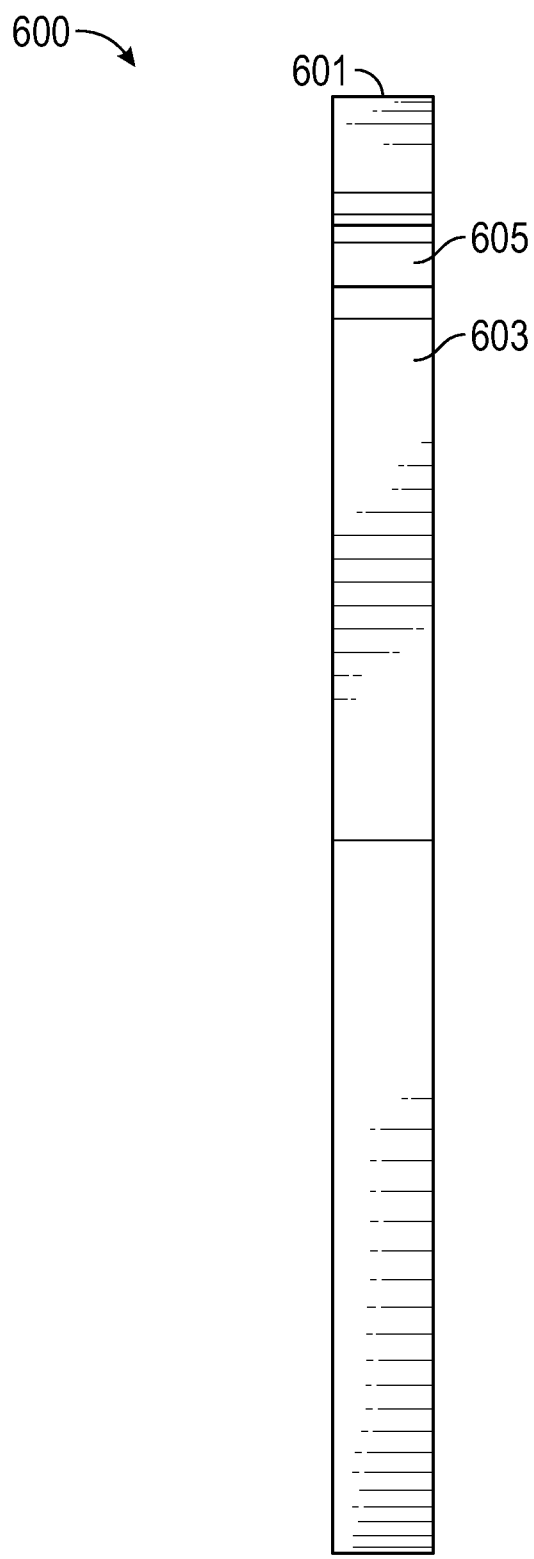
FIG. 6F may depict the clamp of FIG. 6A, shown from a side view.
Figure 6G:
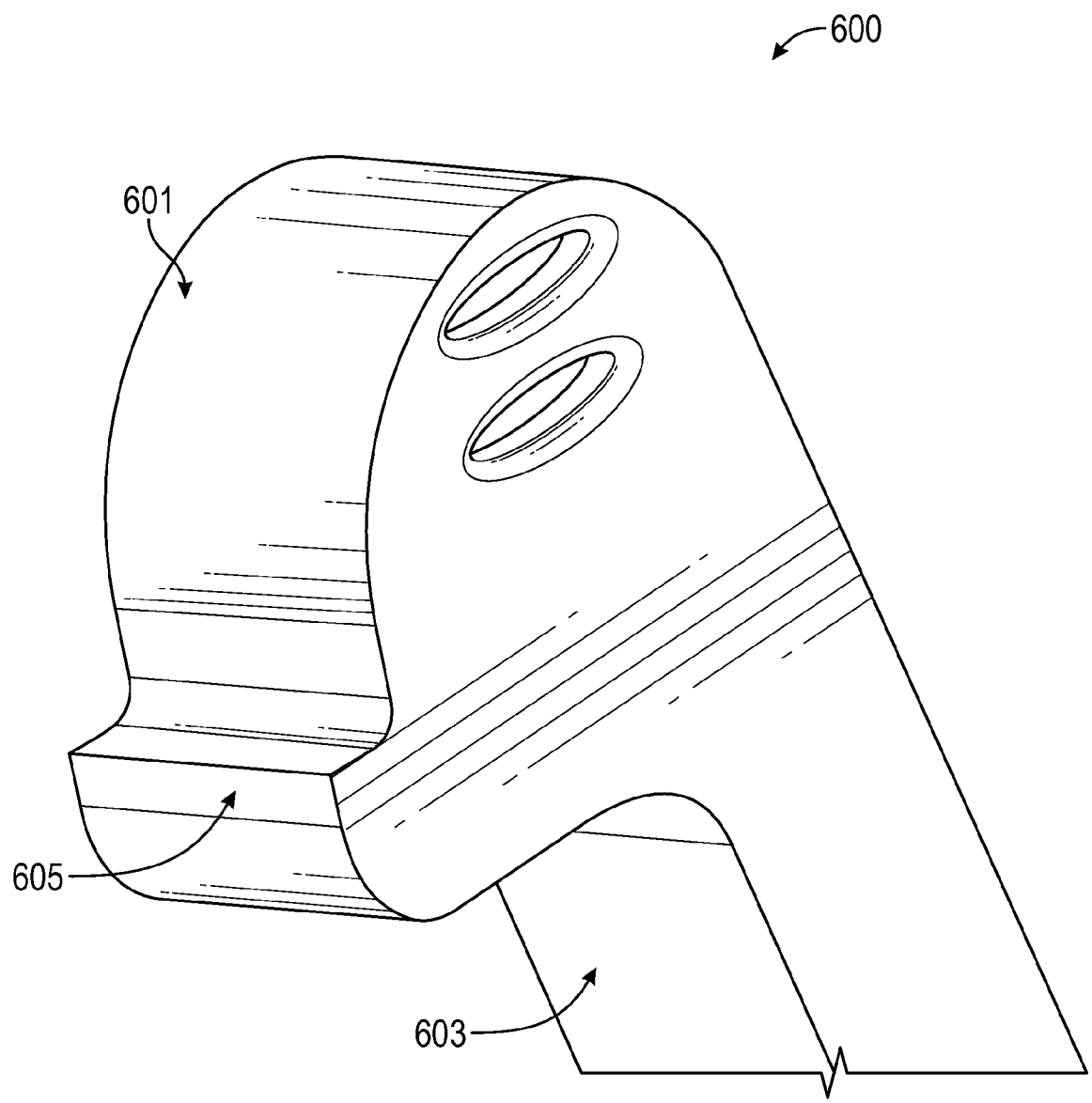
FIG. 6G may depict a close up of one end (a left end) of the clamp of FIG. 6A, shown from a top front perspective view.
Figure 7:
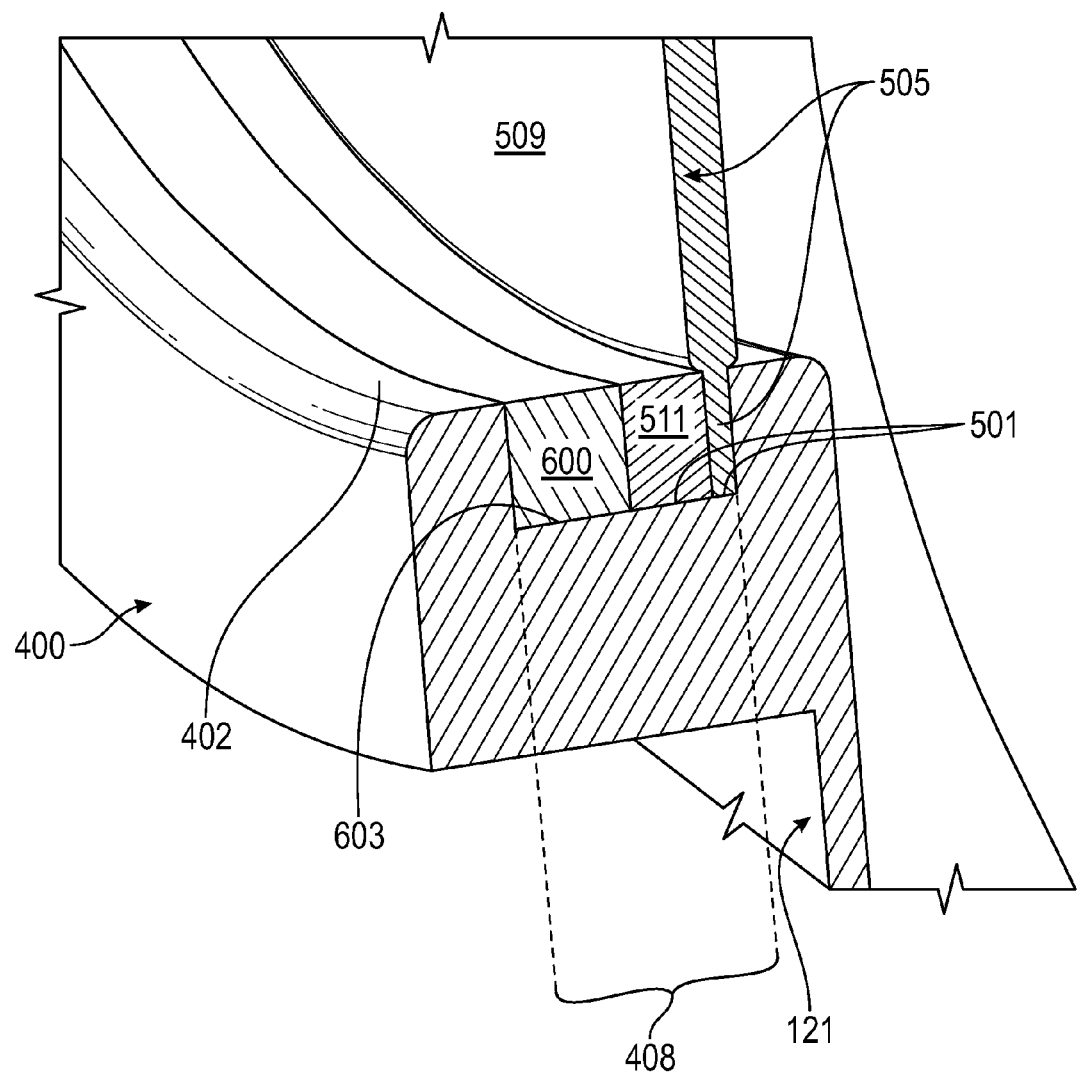
FIG. 7 may depict a cross-sectional view along sectional-line 7-7 that is shown in FIG. 2B.

The FIG. 6 series of figures may comprise FIG. 6A through FIG. 6G. As noted, these FIG. 6 series of figures may focus on showing just clamp 600. FIG. 6A may depict clamp 600, shown from a top front perspective view. FIG. 6B may depict clamp 600, shown from a front view. FIG. 6C may depict clamp 600, shown from a back view. FIG. 6D may depict clamp 600, shown from a top view. FIG. 6E may depict clamp 600, shown from a bottom view. FIG. 6F may depict clamp 600, shown from a side view. FIG. 6G may depict a close up of one end (a left end) of clamp 600, shown from a top front perspective view.

FIG. 7 may depict a cross-sectional view along sectional-line 7-7, that is shown in FIG. 2B. Transverse width cross-sections of neck-gasket-accommodator 400, clamp 600, vessel neck gasket 500 may be seen in FIG. 7, all in their assembled configuration wherein clamp 600 may be assisting in the removable attachment of vessel neck gasket 500 to neck-gasket-accommodator 400 of vessel 120.

In some embodiments, neck-gasket-accommodator 400, vessel neck gasket 500, and clamp 600 may all communicate together forming the primary water tight seal. Compare FIG. 2A against FIG. 3A. In FIG. 2A the primary water tight seal may be intact; whereas, FIG. 3A may show how the primary water tight seal may be formed or is unformed.

In some embodiments, components for forming the primary water tight seal may comprise: neck-gasket-accommodator 400, vessel neck gasket 500, and clamp 600 (or clamp 800, clamp 900, clamp 1000, or clamp 1100). In some embodiments, neck-gasket-accommodator 400 may be a structural member located on a side wall (e.g., wall 121) of vessel 120. In some embodiments, neck-gasket-accommodator 400 may have a contour 402. In some embodiments, contour 402 may tracks an open path that may be below a top rim 122 of the vessel 120. In some embodiments, this open path may be continuous. In some embodiments, extending into the contour 402 may be a receiving-channel 408. See e.g., FIG. 4A. In some embodiments, vessel neck gasket 500 may comprise a mating edge 501. See e.g., FIG. 5A. In some embodiments, at least portions of mating edge 501 may fit within receiving-channel 408. See e.g., FIG. 3A, FIG. 7, FIG. 8, FIG. 9, FIG. 10, and FIG. 11. In some embodiments, the clamp (e.g., 600, 800, 900, 1000, or 1100) may also be a structural member. In some embodiments, the clamp (e.g., 600, 800, 900, 1000, or 1100) may comprise a mating-wall-edge 603. See e.g., FIG. 6A. In some embodiments, at least portions of mating-wall-edge 603 may fit within receiving-channel 408. See e.g., FIG. 3A, FIG. 7, FIG. 8, FIG. 9, FIG. 10, and FIG. 11. In some embodiments, a width of a portion of the clamp (e.g., 600, 800, 900, 1000, or 1100), a width of vessel neck gasket 500, and a width of the receiving-channel 408 may be sized such that when the at least portions of mating-wall-edge 603 and the at least portions of mating edge 501 may be received into receiving-channel 408, the primary water tight seal is formed between a portion of receiving-channel 408 and some portions of vessel neck gasket 500. See e.g., FIG. 3A, FIG. 7, FIG. 8, FIG. 9, FIG. 10, and FIG. 11. In some embodiments, clamp 600 (and other disclosed clamps herein) and vessel neck gasket 500 may be removable from receiving-channel 408. See e.g., FIG. 3A.

In some embodiments, in at least one wall 121 of vessel 120 may be neck-gasket-accommodator 400. In some embodiments, at least one wall 121 of vessel 120 may comprise neck-gasket-accommodator 400. Many figures show neck-gasket-accommodator 400 located in a front wall of face soaking device 100. In some embodiments, neck-gasket-accommodator 400 may be formed in the front wall of vessel 120. See e.g., the FIG. 4 series of figures, such as, FIG. 4A and FIG. 4C.

In some embodiments, neck-gasket-accommodator 400 may comprise contour 402. Contour 402 may generally track an overall shape of neck-gasket-accommodator 400. Contour 402 may comprise one or more surfaces. In some embodiments, such surfaces may face one or more of: each other, face the front of a face soaking device, face the back of a face soaking device, and/or face away from an upper surface of a bottom interior surface of vessel 120. See e.g., FIG. 4A and FIG. 4B.

In some embodiments, neck-gasket-accommodator 400 may comprise contour 402 in at least one wall 121 that runs below rim 122 of vessel 120. In some embodiments, contour 402 begins where a surface of neck-gasket-accommodator 400 first runs below rim 122 and contour 402 continues until ending where the surface of neck-gasket-accommodator 400 runs back up to rim 122. In some embodiments, where contour 402 begins and where contour 402 ends may be separated by horizontal width 404. In some embodiments, contour 338 has maximum vertical length 406 from a height of rim 122 to a lowest point on contour 402. See e.g., FIG. 4B.

In some embodiments, horizontal width 404 may be greater than or equal to a diameter of a neck of the user. In some embodiments, maximum vertical length 406 may be greater than or equal to half of a diameter of the neck of the user. For example, some large adult men may have a neck circumference of about 21 inches, which results in a neck diameter of about 6.69 inches. For example, and without limiting the scope of the present invention, in some embodiments, horizontal width 404 may be 7 to 11 inches. For example, and without limiting the scope of the present invention, in some embodiments, maximum vertical length 406 may be 3.5 to 7 inches.

Neck-gasket-accommodator 400 may comprise a maximum vertical length 406 greater than a second portion of the neck region of the user extending from rim 122 towards at least one base 125 of vessel 120, extending to a bottom most portion of neck-gasket-accommodator 400. See e.g., FIG. 4B. The second portion of the neck region may be a vertical area of a front of the user's neck, i.e. the soft tissue side of the neck, where the neck may contact vessel neck gasket 500. Neck-gasket-accommodator 400 may have a horizontal width 404 greater than a third portion of the neck region of the user centered in a horizontal width (e.g., transverse-width or from right to left) of vessel 120, extending from rim 122 to opposing rim 122 across an opening that neck-gasket-accommodator 400 creates. See e.g., FIG. 4B. The third portion of the neck region may be a horizontal area of a front of the user's neck, i.e. the soft tissue side of the neck, where the neck may contact vessel neck gasket 500.

Note with respect, to the first portion, the second portion, and the third portion of the neck region of the user, the first portion may comprise the second portion and the third portion. That is, the second portion may define a vertical dimension of the first portion and the third portion may define a horizontal dimension of the first portion. For example, and without limiting the scope of the present invention, this first portion of the neck region may be a portion of the neck what may correspond to where an Adam's Apple of a neck may be located; and including up two inches from that Adam's Apple region or a corresponding region on a neck with no Adam's Apple.

In some embodiments, an overall shape of neck-gasket-accommodator 400, with respect to at least one base 125 (see FIG. 1 for at least one base 125) or as viewed from a front of wall 121 that has neck-gasket-accommodator 400, may be shaped suitable to receive vessel neck gasket 500 and the first portion of the neck region of the user when in use in a given face soaking device embodiment (e.g., face soaking device 100). See e.g., FIG. 4B wherein the overall shape of contour 402 of neck-gasket-accommodator 400 may be: curved; rounded; semicircular; semi-elliptical; U-shaped; horseshoe shaped, semi-oval; an arc of a partial circle; an arc of a partial ellipse; an arc of a partial oval; one third to three thirds of a circle; one third to three thirds of an oval; one third to three thirds of an ellipse; and/or the like; e.g., when viewed from the front of face soaking device 100.

In some embodiments, a shape (i.e., the overall shape) of contour 402 as viewed from a front of face soaking device 100 may be selected from the group comprising: curved; rounded; semicircular; semi-elliptical; U-shaped; horseshoe shaped, semi-oval; an arc of a partial circle; an arc of a partial ellipse; an arc of a partial oval; one third to three thirds of a circle; one third to three thirds of an oval; one third to three thirds of an ellipse; a shape approximating an open-ended polygon; and/or the like. See e.g., FIG. 4B.

In some embodiments, the open path of contour 402 may be substantially (i.e., not geometrically perfectly) shaped, as viewed from a front of the side wall, as one of the following: curved; rounded; semicircular; semi-elliptical; U-shaped; horseshoe shaped, semi-oval; an arc of a partial circle; an arc of a partial ellipse; an arc of a partial oval; one third to three thirds of a circle; one third to three thirds of an oval; one third to three thirds of an ellipse; a shape approximating an open-ended polygon; and/or the like.

In some embodiments, the open path of contour 402 may be a regular or an irregular polygon that is not closed (i.e., an open shape) or semi-polygon suitable to that is not closed (i.e., an open shape) suitable to receive bottom portions of vessel neck gasket 500 (e.g., mating edge 501) and the first portion of the neck region of the user when in use. This embodiment is not shown in the figures; however, it should be obvious to one of ordinary skill in the art that the overall shape semi-circular neck-gasket-accommodator 400 shown FIG. 4B may be modified into the open regular or the open irregular polygon or the open semi-polygon of contour 402 and that such a contour may continue to be within the scope of this invention.

Note, in some embodiments, neck-gasket-accommodator 400 may be termed a "gasket-accommodator."

In some embodiments, contour 402 may comprise at least one surface facing away from an upper surface of a bottom interior surface of vessel 120. In some embodiments, along a length of contour 402 may be a receiving-channel 408. See e.g., FIG. 4A and FIG. 7 for a cross-sectional view of this receiving-channel 408. Receiving-channel 408 may be channel or groove cut into contour 402, substantially along a length of contour 402. See e.g., FIG. 4A. A width of receiving-channel 408 may be sized to frictionally fit widths of one or more of: vessel neck gasket 500 (e.g., flexible member 505 plus carrier 511), and/or clamp 600; such that the primary water tight seal is formed. See e.g., FIG. 7.

In some embodiments, a cross-section of the receiving-channel 408 may be substantially (i.e., not geometrically perfectly) shaped as one of the following: curved; rounded; semicircular; semi-elliptical; U-shaped; horseshoe shaped, semi-oval; an arc of a partial circle; an arc of a partial ellipse; an arc of a partial oval; one third to three thirds of a circle; one third to three thirds of an oval; one third to three thirds of an ellipse; or a shape approximating an open-ended polygon. See e.g., FIG. 7, FIG. 8, FIG. 9, FIG. 10, and FIG. 11.

In some embodiments, a direction that receiving-channel 408 extends into contour 402 may be substantially parallel with a major plane of side wall 121. See e.g., FIG. 7, FIG. 8, FIG. 9, FIG. 10, FIG. 11, and FIG. 12E. In some embodiments, the direction that receiving-channel 408 extends into contour 402 may not be perpendicular (nor substantially perpendicular) with the major plane of side wall 121. The major plane of side wall 121 may be substantially collinear with an external surface of side wall 121.

In some embodiments, bottom portions of vessel neck gasket 500 may be configured to fit to (e.g., mate to) contour 402 of neck-gasket-accommodator 400 in at least one wall 121 of vessel 120. In some embodiments, bottom portions of vessel neck gasket 500 may be configured to fit to (e.g., mate to) receiving-channel 408 in contour 402 of neck-gasket-accommodator 400 in at least one wall 121 of vessel 120. See e.g., FIG. 3A, FIG. 4A, FIG. 5A, and FIG. 7. Surface area of mating edge 501 of vessel neck gasket 500 may be equal to, greater than, or less than, as compared against surface area of neck-gasket-accommodator 400. Vessel neck gasket 500 may comprise a mating edge 501 complimentary to at least some surfaces of contour 402 of neck-gasket-accommodator 400 in at least one wall 121 of vessel 120. Vessel neck gasket 500 may comprise a top edge 503. In some embodiments, top edge 503 and mating edge 501 together may define a perimeter of vessel neck gasket 500. In some embodiments, top edge 503 and mating edge 501 may together circumscribe and define a closed shape for vessel neck gasket 500. In some embodiments, top edge 503 and mating edge 501 may each curve for at least some portion of the given edge. In some embodiments, a radius of curvature for top edge 503 may be different for a radius of curvature for edge 501. See e.g., FIG. 5A. In some embodiments, top edge 503 may be accommodative to receiving the first portion of the neck region of the user. In some embodiments, when vessel neck gasket 500 may be attached to neck-gasket-accommodator 400, e.g., as in the FIG. 2 series of figures (e.g., FIG. 2A), some portions of top edge 503 may extend above rim 122 (e.g., FIG. 2B). In some embodiments, mating edge 501 of vessel neck gasket 500 may be attached to contour 402 of neck-gasket-accommodator 400 by a vessel neck gasket attachment means. In some embodiments, mating edge 501 of vessel neck gasket 500 may be received into receiving-channel 408 of contour 402.

In some embodiments, the vessel neck gasket attachment means may comprise clamp 600. Or in some embodiments, mating edge 501 of vessel neck gasket 500 may be attached to either an exterior wall surface or an interior wall surface of at least one wall 121, at a fixed distance from contour 402 of neck-gasket-accommodator 400 by the vessel neck gasket attachment means. For example, and without limiting the scope of the present invention, in some embodiments, the fixed distance may be one inch or less. In other embodiments, the fixed distance may be other distances.

In some embodiments, vessel neck gasket 500 may be removable from vessel 120. In some embodiments, vessel neck gasket 500 may be removable from neck-gasket-accommodator 400. Such embodiments may facilitate switching out vessel neck gasket 500 in the event of wear and tear and/or damage to an installed vessel neck gasket 500. In some other embodiments, vessel neck gasket 500 may not be removed from vessel 120 once installed.

In some embodiments, vessel neck gasket 500 may be a subassembly comprising two parts: a flexible member 505 and a carrier 511. In some embodiments, vessel neck gasket 500 may comprise flexible member 505 and carrier 511. In some embodiments, flexible member 505 and carrier 511 may be attached to each other. See e.g., FIG. 5A.

In some embodiments, flexible member 505 may be substantially planar with an internal surface 507 (see FIG. 5D) and an external surface 509 (see FIG. 5A) disposed opposite of internal surface 507. Portions of either external surface 509 or internal surface 507 may form the secondary water tight seal with the neck region, when the user rests their neck against portions of vessel neck gasket 500. In some embodiments, a portion of internal surface 507 may physically contact some of the liquid when the liquid may be held within the internal volume of vessel 120.

In some embodiments, flexible member 505 may be a flexible sheet. In some embodiments, this flexible sheet may be shaped generally with mating edge 501 that is complimentary to cover portions (e.g., receiving-channel 408) of neck-gasket-accommodator 400 of vessel 120. In some embodiments, this flexible sheet may be shaped generally with mating edge 501 that is complimentary to cover portions of receiving-channel 408. In some embodiments, this flexible sheet may comprise a gasket along the bottom of the sheet. In some embodiments, this gasket may be mating edge 501. See e.g., FIG. 5A and FIG. 5F.

In some embodiments, flexible member 505 may be substantially constructed of one or more materials (i.e., materials of construction) suitable for forming water tight seals against human skin (or against an exterior portion of a terrestrial vertebrates body) and/or against the vessel (e.g. vessel 120), and/or suitable for being comfortable when touching human skin. In some embodiments, flexible member 505 may be constructed of one or more of elastomers comprising silicone, rubber, neoprene, nitrile, vinyl, polyethylene, polypropylene, and/or any other material suitable for forming water tight seals against human skin and/or against the vessel (e.g. vessel 120), and/or suitable for being comfortable when touching human skin. In some embodiments, the rubber may be natural rubber. In some embodiments, the rubber may be synthetic, including latex free. In some embodiments, flexible member 505 may be compressible. For example, and without limiting the scope of the present invention, when vessel neck gasket 500 may be attached to neck-gasket-accommodator 400, portions of internal surface 507 and external surface 509 that may be residing within receiving-channel 408 of neck-gasket-accommodator 400, may be compressed; see e.g., FIG. 7. Such compression of portions of flexible member 505 within receiving-channel 408 may aid in forming the primary water tight seal. Compare, FIG. 5F and FIG. 5G may show flexible member 505 in a non-compressed state. In some embodiments, portions of flexible member 505 may be compressed by 5% to 95% as compared to non-compressed states of flexible member 505.

In some embodiments, a shape (e.g., an overall shape) of receiving-channel 408 as viewed in a cross-section may be selected from the group comprising: one third to three thirds of a circle; one third to three thirds of an oval; one third to three thirds of an ellipse; a "U" shape, a horseshoe shape; a regular polygon open at a top (with or without rounded corners), an irregular polygon open at a top (with or without rounded corners); a semi-polygon open at a top (with or without rounded corners); and/or the like; with an arc of the partial circle, partial oval, partial ellipse, or the horseshoe shape oriented downwards towards at least one base 125. See e.g., FIG. 7, FIG. 8, FIG. 9, FIG. 10, and FIG. 11.

In some embodiments, internal surface 507 and external surface 509 may be constructed of different elastomers. That is, flexible member 505 may be a laminate or comprised of planar layers. Internal surface 507 may be constructed of an elastomer with a focus on water impermeability. External surface 509 may be constructed of an elastomer with a focus on comfort to the user, i.e., an elastomer with a soft outer surface and/or a non-tacky outer surface. Such two different elastomers may be joined into a single flexible composite member of flexible member 505. The means for joining internal surface 507 to external surface 509 may be by solvent bonding, heat welding, ultrasonic welding, chemical adhesive/sealant, mechanical fasteners (e.g., stitching and/or staples, or the like), and/or the like.

In some embodiments, flexible member 505 may be manufactured by die cutting, stamping, molding, and/or 3D printing.

In some embodiments, carrier 511 may be attached to flexible member 505. The means for joining carrier 511 to flexible member 505 may be by solvent bonding, heat welding, ultrasonic welding, chemical adhesive/sealant, mechanical fasteners (e.g., stitching and/or staples, or the like), and/or the like. See e.g., FIG. 5A and FIG. 5B. In some embodiments, carrier 511 may be integral with flexible member 505. In some embodiments, carrier 511 may be a structural member. In some embodiments, carrier 511 may be rigid to semi-rigid. In some embodiments, carrier 511 may be substantially constructed from one or more thermoformed plastics, metal, wood, composite, laminate, and/or the like. In some embodiments, carrier 511 may have a higher durometer as compared against a durometer of flexible member 505. In some embodiments, carrier 511 may impart structural rigidity to bottom portions of flexible member 505, which may facilitate loading or feeding of bottom portions of vessel neck gasket 500 into neck-gasket-accommodator 400 receiving-channel 408. See e.g., FIG. 3A and FIG. 3B. In some embodiments, carrier 511 may have a shape that is complimentary to bottom surfaces of flexible member 505, such as mating edge 501. In some embodiments, both carrier 511 and flexible member 505 may share mating edge 501. See e.g., FIG. 3A, FIG. 5A, FIG. 5B, FIG. 7, FIG. 8, FIG. 9, FIG. 10, and FIG. 11.

In some embodiments, carrier 511 may be shaped complimentary to a shape of the open path of contour 402. In some embodiments, mating edge 501 may be shaped complimentary to a shape of receiving-channel 408. See e.g., FIG. 3A, FIG. 7, FIG. 8, FIG. 9, FIG. 10, and FIG. 11.

In some embodiments, carrier 511 may be manufactured by die cutting, stamping, molding, extrusion, and/or 3D printing.

In some embodiments, the vessel neck gasket attachment means may be selected from one or more of: a friction fit, heat welding, ultrasonic welding, solvent bonding, chemical adhesives and/or sealants, mechanical fasteners, and/or the like. Use of clamp 600 may an example of a frictional fit and/or a type of mechanical fastener. Recall, the vessel neck gasket attachment means may be how vessel neck gasket 500 may be attached to neck-gasket-accommodator 400.

In some embodiments, an embodiment of face soaking device 100 may comprise at least these elements: vessel neck gasket 500, clamp 600, and vessel 120 with neck-gasket-accommodator 400 of at least one wall 121 of vessel 120. In some embodiments, a vessel neck gasket subassembly may comprise at least these parts: vessel neck gasket 500, clamp 600, and neck-gasket-accommodator 400. Neck-gasket-accommodator 400 may be a portion or region of a given vessel embodiment, such as vessel 120 embodiments.

In some embodiments vessel neck gasket 500 may be attached to neck-gasket-accommodator 400 by use of clamp 600. See e.g., FIG. 3A, FIG. 3B, and FIG. 7. In some embodiments such an attachment may form the primary water tight seal. In some embodiments clamp 600 may be shaped to complimentary fit to neck-gasket-accommodator 400, with a portion of vessel neck gasket 500 sandwiched between clamp 240 and contour 402 of neck-gasket-accommodator 400, forming the primary water tight seal. See e.g., FIG. 3A, FIG. 3B, and FIG. 7. In some embodiments, contour 402 may comprise at least one surface facing away from an upper surface of a bottom interior surface of vessel 120. The Bottom interior surface may be an interior surface of vessel 120. A width of receiving-channel 408 (of neck-gasket-accommodator 400) may be sized to frictionally fit widths of one or more of: vessel neck gasket 500 (i.e., flexible member 505 plus carrier 511), and/or clamp 600; such that the primary water tight seal is formed. See e.g., FIG. 7.

In some embodiments, clamp 600 fit attachment to contour 402 of neck-gasket-accommodator 400 may be removable. In some embodiments, at least some portions of clamp 600 may fit into portions of receiving-channel 408. In some embodiments, clamp 600 fit attachment to contour 402 of neck-gasket-accommodator 400 may be a frictional fit. In some embodiments, clamp 600 fit attachment to contour 402 of neck-gasket-accommodator 400 may be from one or more snap fits.

In some embodiments, clamp 600 may be constructed (or substantially) of a semirigid to rigid material of construction. For example, and without limiting the scope of the present invention, clamp 600 may be substantially constructed of one or more of a thermoformed plastic, metal, wood, composite, laminate, and/or the like. In some embodiments, clamp 600 and carrier 511 may be substantially constructed of the same types of materials. In some embodiments, clamp 600 may be manufactured via die cutting, stamping, molding (e.g., injection molding), extrusion, and/or 3D printing. In some embodiments, at least some of the above characteristics (e.g., rigidity and/or materials of construction) of clamp 600 may be shared with clamps 800, 900, 1000, and 1100. However, as show, clamps 800, 900, 1000, and 1100 may have different geometry and/or structures from clamp 600.

A FIG. 6A and FIG. 6G may depict snap latch structure illustrating how clamp 600 (of the FIG. 3 series) may removably couple with neck-gasket-accommodator 400. Such snap latch connections may work to assist in removably coupling clamp 600 to neck-gasket-accommodator 400.

In some embodiments, neck-gasket-accommodator 400 may comprises two opposing opening wall-edges 410. In some embodiments, the two opposing opening wall-edges 410 may define where neck-gasket-accommodator 400 begins. See e.g., FIG. 4A and FIG. 4C. In some embodiments, each opening wall-edge 410 (e.g., left and right) may be separated from the other by at least the at least horizontal width 404 of neck-gasket-accommodator 400 (see e.g., FIG. 4B for horizontal width 404). In some embodiments, each opening wall-edge 410 may descend downwards in a direction towards at least one base 125 from rim 122. In some embodiments, each opening wall-edge 410 may be substantially flat (i.e., a substantially flat surface). See e.g., FIG. 4A and FIG. 4C.

In some embodiments, clamp 600 may comprise two terminal ends 601 disposed opposite of each other. See e.g., FIG. 6A, FIG. 6B, and FIG. 6C. In some embodiments, each terminal end 601 may comprise a mating-wall-edge 603. In some embodiments, clamp 600 may comprise mating-wall-edges 603. In some embodiments, at least some portion of a given mating-wall-edge 603 may be located below and/or proximate (e.g., within three inches in some embodiments) to a given terminal end 601. See e.g., FIG. 6A which may depict one such mating-wall-edge 603; e.g., a right mating-wall-edge 603 from the perspective of the user looking at the front of face soaking device 100; wherein a right mating-wall-edge 603 may be a mirror image of the left mating-wall-edge 603.

In some embodiments, each mating-wall-edge 603 may be paired with a respective opening wall-edge 410, such that mating-wall-edge 603 paired to a given opening wall-edge 410 may be complimentary to each other, when clamp 600 may be removably coupled to neck-gasket-accommodator 400. See e.g., FIG. 3A and FIG. 3B. In some embodiments, each mating-wall-edge 603 may be paired with a respective opening wall-edge 410, such that mating-wall-edge 603 paired to the respective opening wall-edge 410 may be substantially parallel to each other, when clamp 600 may be removably coupled to neck-gasket-accommodator 400. For example, and without limiting the scope of the present invention, left opening wall-edge 410 may be paired with left mating-wall-edge 603. For example, and without limiting the scope of the present invention, right opening wall-edge 410 may be paired with right mating-wall-edge 603. In some embodiments, each mating-wall-edge 603 may be substantially flat to compliment a substantially flat region on corresponding (paired) opening wall-edge 410. See e.g., FIG. 3A and FIG. 3B.

In some embodiments, when left opening wall-edge 410 may be paired with left mating-wall-edge 603 and right opening wall-edge 410 may be paired with right mating-wall-edge 603 each respective pairing may be a friction fit between the paired and complimentary surfaces.

In some embodiments, each mating-wall-edge 603 may terminate in a snap latch 605. See e.g., FIG. 6A, FIG. 6B, and FIG. 6G. In some embodiments, each opening wall-edge 410 may comprise a pocket 412, which may be an indenture extending into the given opening wall-edge 410. Each such pocket 412 may be sized to removably fit a respective snap latch 605. In some embodiments, each snap latch 605 may be paired with a respective pocket 412 such that the paired snap latch 605 may removably snap into paired pocket 412 to form a removable snap latch connection at each of the two respective pairings. See e.g., FIG. 3A and FIG. 3B. In some embodiments, a paired snap latch 605 may comprise a protrusion that may be removably engage the paired pocket 412. See e.g., FIG. 3A and FIG. 3B.

In some embodiments, release of each removable snap latch connection (left and right) may be accomplished by the user squeezing each terminal end 601 towards each other, which may disengage a given paired snap latch 605 from the paired pocket 412. In some embodiments, release of clamp 600 from neck-gasket-accommodator 400 may also require the user to pull clamp 600 upwards or away from neck-gasket-accommodator 400. In some embodiments, there may be structure located proximate (e.g., within three inches) to each terminal end 601; wherein such structure may aid or may facilitate removal (i.e., release) of clamp 600 from neck-gasket-accommodator 400. For example, and without limiting the scope of the present invention, in some embodiments, this structure may be indentures, such as, divots, to removably receive a tool for pushing the two terminal ends 601 towards each other. See e.g., FIG. 6A, FIG. 6B, FIG. 6C, FIG. 6G, FIG. 2A, FIG. 2B, FIG. 2D, FIG. 3A, and FIG. 3B. For example, and without limiting the scope of the present invention, in some embodiments, this structure may be removably engage pressing fingers from the user for pushing (e.g., squeezing) the two terminal ends 601 towards each other.

Some embodiments may be characterized as a "flexible detachable vessel cover" that may comprise: (1) vessel 120 having a top opening and capable of holding the liquid; wherein vessel 120 has neck-gasket-accommodator 400; and (2) a flexible sheet (e.g., vessel neck gasket 500); wherein the flexible sheet that may be shaped generally to cover gasket-accommodator 400 of vessel 120; wherein the flexible sheet has a gasket (e.g., mating edge 501) along the bottom of the flexible sheet; and wherein the bottom of the gasket and a top of gasket-accommodator 400 of vessel 120 are arranged to mate tightly with one another to form the primary water tight seal.

FIG. 8, FIG. 9, FIG. 10, and FIG. 11 may depict views and embodiments comparable against those shown in FIG. 7. FIG. 8, FIG. 9, FIG. 10, and FIG. 11 may depict additional embodiments of the clamp, i.e., of clamp 800, clamp 900, clamp 1000, and clamp 1100, respectively, wherein such clamps may frictionally and removably snap onto an exterior vertical portion of neck-gasket-accommodator 400. See e.g., FIG. 8, FIG. 9, FIG. 10, and FIG. 11. Compare the clamps of FIG. 8, FIG. 9, FIG. 10, and FIG. 11 against clamp 600 of FIG. 7.

In some embodiments of face soaking device 100, the clamp may be selected from: clamp 600, clamp 800, clamp 900, clamp 1000, clamp 1100, or the like.

Figure 8:
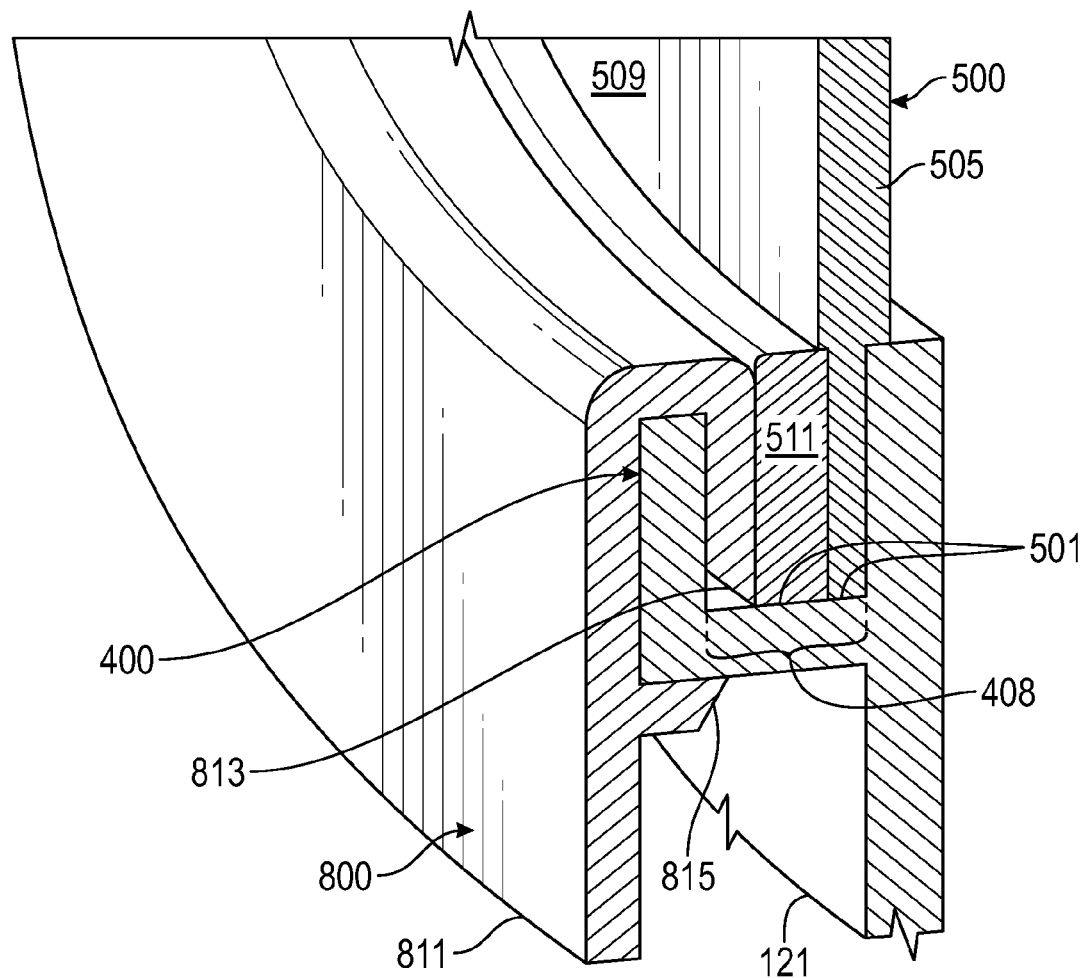
FIG. 8 may depict a cross-sectional view of the neck-gasket-accommodator, the vessel neck gasket, and an additional embodiment of the clamp.
Figure 9:
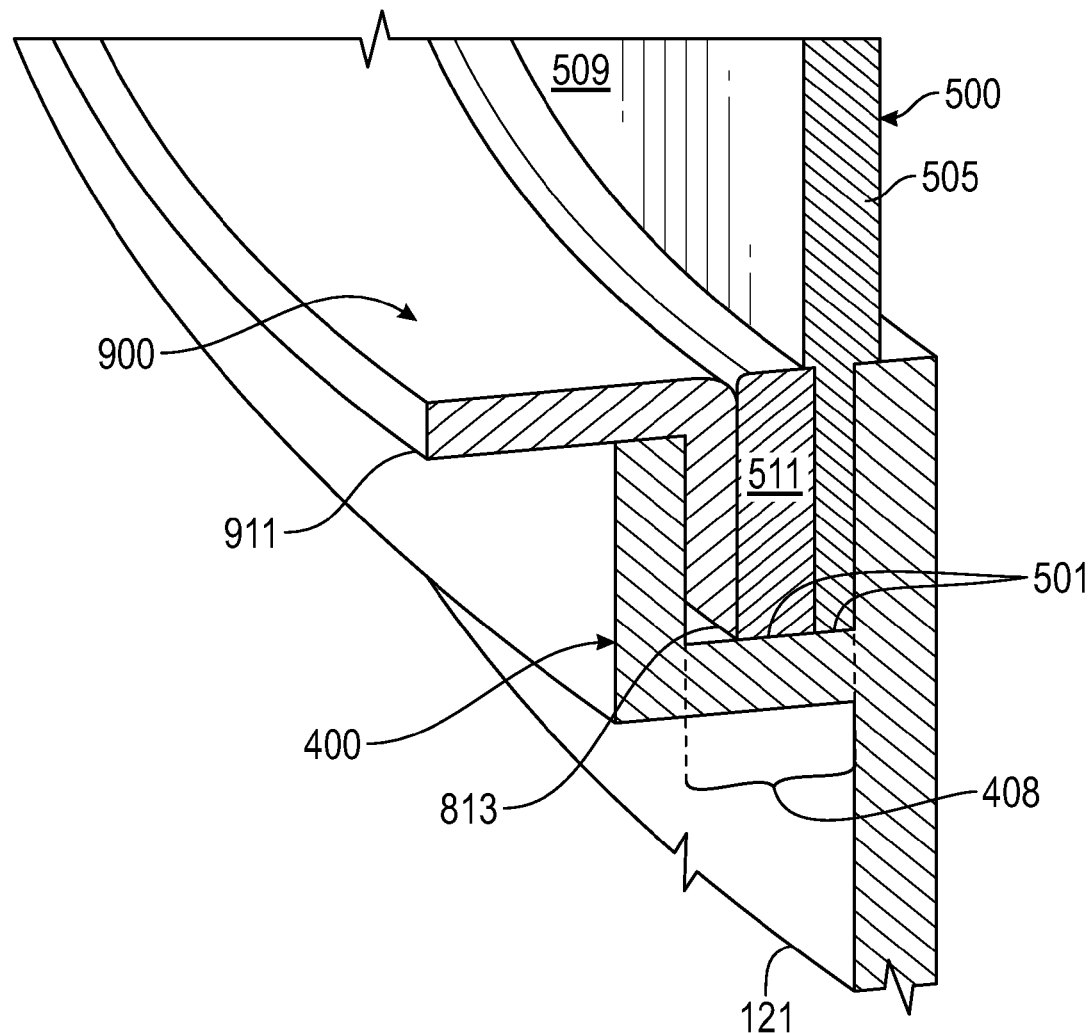
FIG. 9 may depict a cross-sectional view of the neck-gasket-accommodator, the vessel neck gasket, and an additional embodiment of the clamp.
Figure 10:
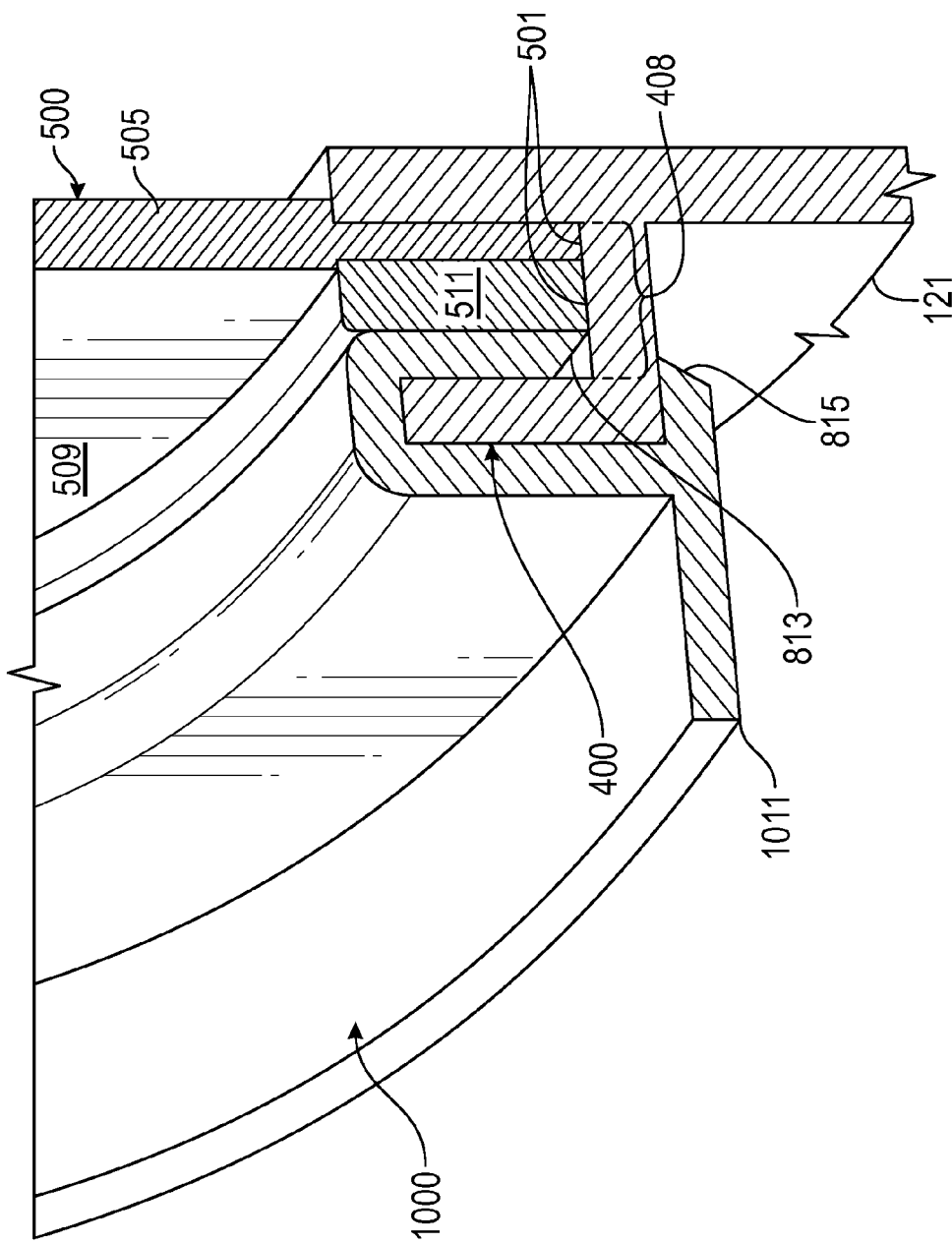
FIG. 10 may depict a cross-sectional view of the neck-gasket-accommodator, the vessel neck gasket, and an additional embodiment of the clamp.
Figure 11:
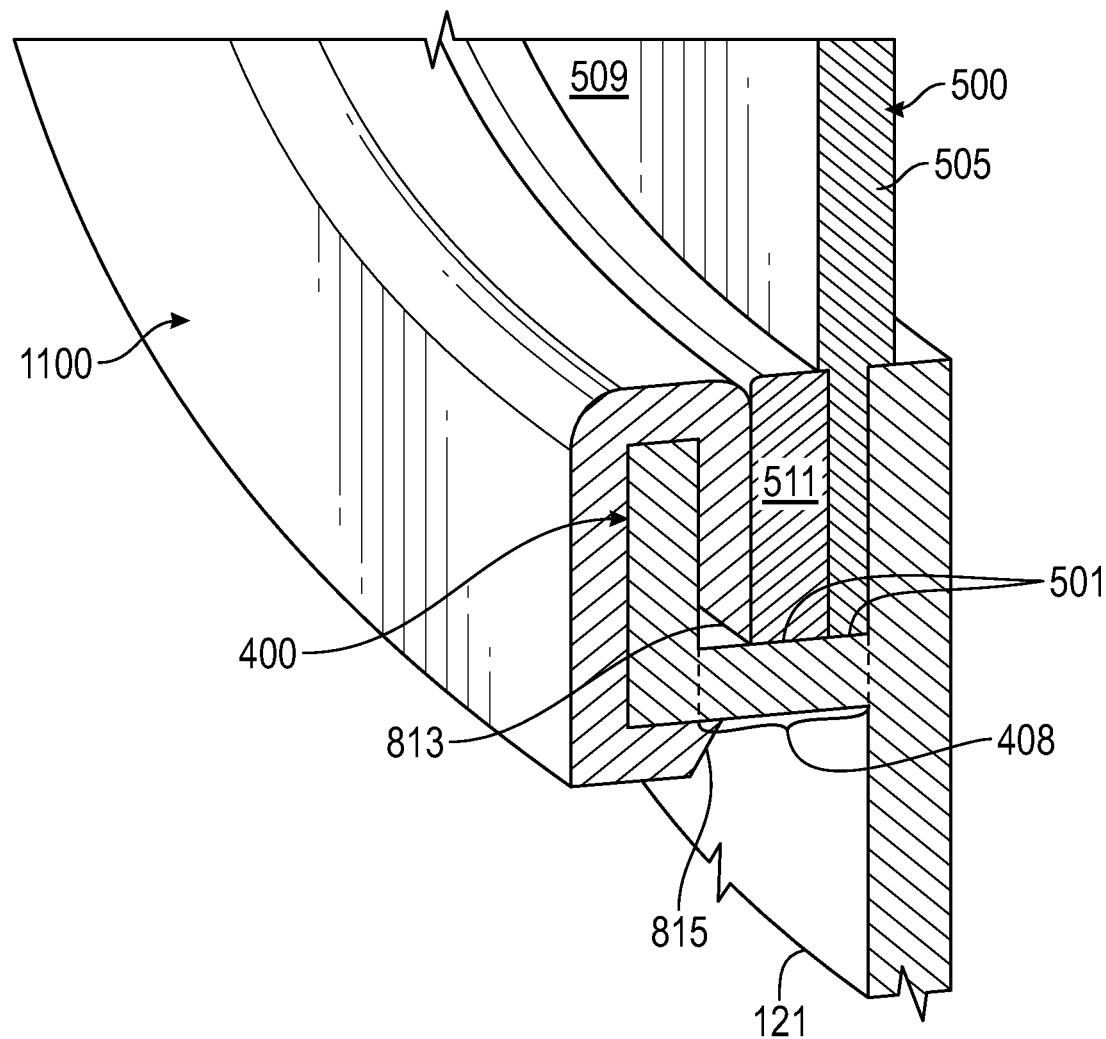
FIG. 11 may depict a cross-sectional view of the neck-gasket-accommodator, the vessel neck gasket, and an additional embodiment of the clamp.

In FIG. 8, clamp 800 may removably and frictionally snap around the exterior vertical portion of neck-gasket-accommodator 400. In some embodiments, to assist with this removable and frictional snap lock, clamp 800 may comprise a relatively short protrusion, tab 815, which may protrude substantially perpendicularly from a vertical direction of clamp 800, such that tab 815 may removably engage a bottom and outward edge of neck-gasket-accommodator 400. In some embodiments, tab 815 may extend from the given clamp (e.g., clamp 800) in a direction that may be substantially perpendicular from the major plane of side wall 121. In some embodiments, tab 815 may snap onto a corner of the neck-gasket-accommodator 400. In some embodiments, when a given clamp (e.g., clamp 800) may be attached to neck-gasket-accommodator 400, tab 815 may protrude towards vessel 120. See e.g., FIG. 8. Tab 815 may have a length that is less than the vertical lengths of clamp 800. Tab 815 may be an integral structure of clamp 800. In some embodiments, clamp 1000 and clamp 1100 may also comprise such a tab 815. See e.g., FIG. 10 and FIG. 11.

Continuing discussing FIG. 8, in some embodiments, clamp 800 may also comprise finger-pull 811. Finger-pull 811 may be a vertically oriented finger pull, allowing the user to lift under finger-pull 811 when removing clamp 800 from neck-gasket-accommodator 400. In some embodiments, finger-pull 811 may be a vertical extension of clamp 800, extending below and beyond tab 815, and below where neck-gasket-accommodator 400 ends. Finger-pull 811 may be an integral structure of clamp 800. In cross-section as shown in FIG. 8, clamp 800 may resemble a stylized letter "f"; wherein the terminal of the ascender curves around to point towards receiving-channel 408; the stem descends into finger-pull 811; and there may only one arm being that of tab 815.

Clamp 900 (shown in FIG. 9) and clamp 1000 (shown in FIG. 10) may each also comprise similar finger pulls, finger-pull 911 and finger-pull 1011, respectively. Each of finger-pull 911 and finger-pull 1011, may extend substantially perpendicularly away from wall 121 shown in FIG. 9 and in FIG. 10, respectively. See e.g., FIG. 9 and FIG. 10. A crosssection of clamp 900 may be "L" shaped, where one leg of the "L" is for removable insertion into receiving-channel 408 and the other leg of the "L" is finger-pull 911. See FIG. 9. A cross-section of clamp 1000 may resemble an upside down letter "J." With clamp 1000, finger-pull 1011 and tab 815 may be collinear but extending in opposite directions of each other, with finger-pull 1011 extending away from vessel 120 and with tab 815 extending towards vessel 120. See FIG. 10.

Although all three finger pulls (e.g., finger-pull 811, finger-pull 911, and, finger-pull 1011) may be structurally different, each may serve a similar or same purpose, in aiding the user in removing the given clamp from neck-gasket-accommodator 400, by providing explicit structure to be engaged by fingers for pulling upwards and away from vessel 120.

Additionally, clamp 800 may comprise chamfer 813, which may be located a terminal portion of clamp 800 that is removably retained in receiving-channel 408. Chamfer 813 may be a chamfer and may aid in inserting clamp 800 into receiving-channel 408 and against portions of vessel neck gasket 500 that also may removably reside within receiving-channel 408. Clamp 600, clamp 900, clamp 1000, and clamp 1100 may also comprise such a chamfer 813. Chamfer 813 may also aid use of a given finger pull (e.g., finger-pull 811, finger-pull 911, and, finger-pull 1011), by providing a small region of void space within receiving-channel 408, such that when the user pulls on the given finger pull, the terminal end of the clamp within receiving-channel 408 may articulate (i.e., pivot) into this void region of the given receiving-channel 408.

Note, with respect to various clamps disclosed herein, such as, but not limited to, clamp 600, clamp 800, clamp 900, clamp 1000, and clamp 1100, these clamps may function technically as a wedge, when portions of such clamps may be removably inserted in receiving-channel 408, creating opposing lateral compression forces against portions of vessel neck gasket 500 (e.g., carrier 511 and flexible member 505) within receiving-channel 408, as well as against wall(s) of receiving-channel 408, which may be surfaces of contour 402. These lateral compression forces may compress portions of flexible member 505 as noted herein, which may aid in creating the primary water tight seal. See e.g., FIG. 7, FIG. 8, FIG. 9, FIG. 10, and FIG. 11. Additionally, portions of these clamps (e.g., clamp 600, clamp 800, clamp 900, clamp 1000, and clamp 1100), e.g., mating-wall-edge 603, which may be structure present on each of these clamps, may press against portions of receiving-channel 408, such as opposing opening wall-edge 410; and in this functional capacity these clamps may be acting as a clamp (as in a device that presses together so as to hold firmly) and/or as a wedge. That is, when any of these clamps may be inserted into receiving-channel 408, receiving-channel 408 and the portions of the clamp may be pressing against each other.

Figure 12A:
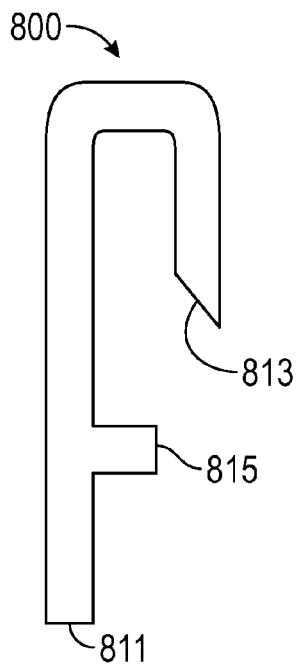
FIG. 12A may show that a clamp embodiment may resemble a letter "f" in cross-section.
Figure 12B:
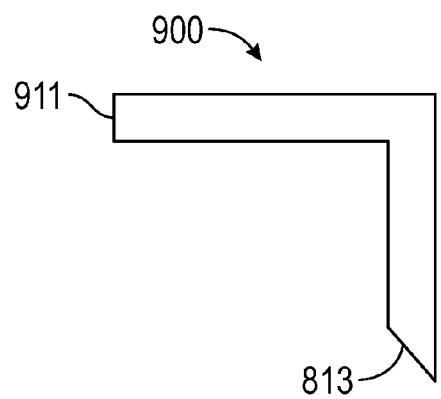
FIG. 12B may show that a clamp embodiment may resemble a letter "L" in cross-section.
Figure 12C:
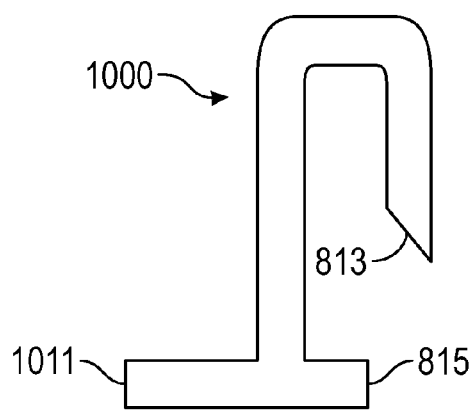
FIG. 12C may show that a clamp embodiment may resemble a letter "J" in cross-section.
Figure 12D:
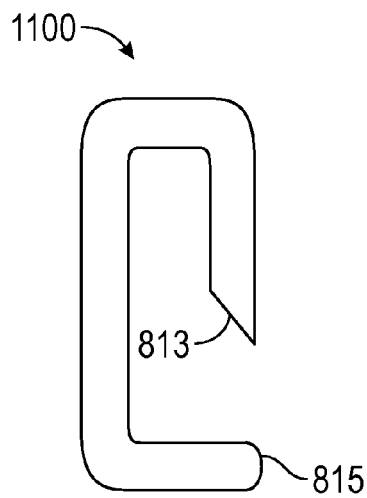
FIG. 12D may show that a clamp embodiment may resemble a letter "C" in cross-section.
Figure 12E:
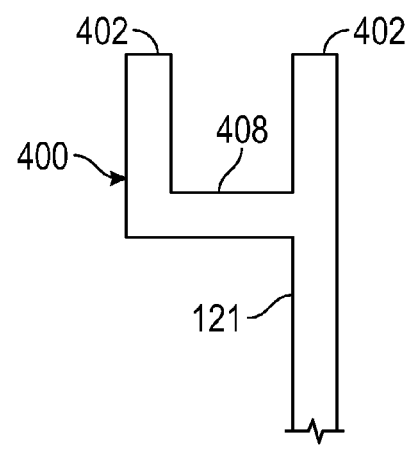
FIG. 12E may depict a cross-sectional view of a neck-gasket-accommodator.

FIG. 12A through FIG. 12D may depict cross-sectional views of various clamps, such as clamp 800 in FIG. 12A; clamp 900 in FIG. 12B; clamp 1000 in FIG. 12C; and clamp 1100 in FIG. 12D. FIG. 12E may depict a cross-sectional view of neck-gasket-accommodator 400; which may comprise receiving-channel 408 that may receive portions (e.g., portions with chamfer 813) of the various clamps. FIG. 12A may show that clamp 800 may resemble a letter "f" in cross-section. FIG. 12B may show that clamp 900 may resemble a letter "L" in cross-section. FIG. 12C may show that clamp 1000 may resemble a letter "J" in cross-section. FIG. 12D may show that clamp 1100 may resemble a letter "C" in cross-section.

In some embodiments, a region comprising neck-gasket-accommodator 400 and comprising where neck-gasket-accommodator joins the side wall 121; wherein this region, in cross-section, resembles an Arabic number "4." See e.g., FIG. 12E, FIG. 7, FIG. 8, FIG. 9, FIG. 10, and FIG. 11.

In some embodiments, some face soaking device 100 component parts may be substantially constructed of one or more thermoplastics suitable for injection molding and/or 3D printing. For example, and without limiting the scope of the present invention, some face soaking device 100 component parts may be substantially constructed of one or more materials of acrylonitrile-butadiene styrene (ABS), polyvinyl chloride (PVC), polycarbonate, nylon, polypropylene, polyethylene (e.g., HDPE), elastomers, rubbers, silicones, fiberglass, and/or the like.

Note with respect to the materials of construction, it is not desired nor intended to thereby unnecessarily limit the present invention by reason of such disclosure.

Note, in some embodiments, such component parts as flexible member 505, carrier 511, and/or the various clamps (e.g., clamp 600 and clamp 900) may be manufactured with reliable and quality manufacturing methods of die cutting (stamping) which may be considerably less expensive as compared against creating the tooling for molds of such parts. And other clamp embodiments (e.g., clamp 600, clamp 800, clamp 900, clamp 1000, and clamp 1100), may be manufacturing by custom extrusion with cuts at appropriate lengths, which may be a reliable and quality manufacturing method that is less expensive than creating the tooling for molds of such parts.

Face soaking devices have been described. The foregoing description of the various exemplary embodiments of the invention has been presented for the purposes of illustration and disclosure. It is not intended to be exhaustive or to limit the invention to the precise form disclosed. Many modifications and variations are possible in light of the above teaching without departing from the spirit of the invention.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. Components for forming a primary water tight seal comprising:
   a neck-gasket-accommodator that is a first structural member located on a side wall of a vessel; wherein the neck-gasket-accommodator has a contour that tracks an open path that is below a top rim of the vessel; wherein extending into the contour is a receiving-channel;
   a vessel neck gasket that is substantially flexible and planar, wherein the vessel neck gasket has a mating edge; wherein at least portions of the mating edge fit within the receiving-channel; and
   a clamp that is a second structural member with a mating-wall-edge; wherein at least portions of the mating-wall-edge fit within the receiving-channel;
   wherein a width of a portion of the clamp, a width of the vessel neck gasket, and a width of the receiving-channel are sized such that when the at least portions of the mating-wall-edge and the at least portions of the mating edge are received into the receiving-channel, the primary water tight seal is formed between a portion of the receiving-channel and some portions of the vessel neck gasket.

2. The components for forming the primary water tight seal according to claim 1, wherein the open path of the contour is continuous.

3. The components for forming the primary water tight seal according to claim 1, wherein the open path of the contour is substantially shaped, as viewed from a front of the side wall, as one of the following: curved; rounded; semi-circular; semi-elliptical; U-shaped; horseshoe shaped; semi-oval; an arc of a partial circle; an arc of a partial ellipse; an arc of a partial oval; one third to one half of a circle; one third to one half of an oval; one third to one half of an ellipse; or a shape approximating an open-ended polygon.

4. The components for forming the primary water tight seal according to claim 1, wherein a cross-section of the receiving-channel is substantially shaped as one of the following: curved; rounded; semicircular; semi-elliptical; U-shaped; horseshoe shaped; semi-oval; an arc of a partial circle; an arc of a partial ellipse; an arc of a partial oval; one third to one half of a circle; one third to one half of an oval; one third to one half of an ellipse; or a shape approximating an open-ended polygon.

5. The components for forming the primary water tight seal according to claim 1, wherein a direction that the receiving-channel extends into the contour is substantially parallel with a major plane of the side wall.

6. The components for forming the primary water tight seal according to claim 1, wherein the components for forming the primary water tight seal further comprises a region; wherein the region comprises the neck-gasket-accommodator and where the neck-gasket-accommodator joins the side wall this region, in cross-section, resembles an Arabic number "4".

7. The components for forming the primary water tight seal according to claim 1, wherein the vessel neck gasket comprises a flexible member and a carrier; wherein the flexible member is flexible and substantially planar; wherein the carrier is a third structural member that provides some rigidity to the flexible member; wherein the carrier is attached to the flexible member; wherein both the carrier and the flexible member share the mating edge.

8. The components for forming the primary water tight seal according to claim 7, wherein the flexible member is substantially elastomeric.

9. The components for forming the primary water tight seal according to claim 8, wherein when the at least portions of the mating-wall-edge and the at least portions of the mating edge are received into the receiving-channel, portions of the flexible-member within the receiving-channel are compressed which contributes to forming the primary water tight seal.

10. The components for forming the primary water tight seal according to claim 7, wherein the flexible member comprises a top edge wherein at least a portion of the top edge extends beyond the top rim of the vessel when the vessel neck gasket is attached to the receiving-channel; wherein the top edge and the mating edge of the flexible member define a closed shape for the flexible member.

11. The components for forming the primary water tight seal according to claim 7, wherein the carrier is rigid to semi-rigid.

12. The components for forming the primary water tight seal according to claim 7, wherein the carrier is shaped complimentary to a shape of the open path of the contour.

13. The components for forming the primary water tight seal according to claim 1, wherein the mating edge is shaped complimentary to a shape of the receiving-channel.

14. The components for forming the primary water tight seal according to claim 1, wherein the mating-wall-edge of the clamp has a chamfer to facilitate insertion into the receiving-channel.

15. The components for forming the primary water tight seal according to claim 1, wherein the clamp terminates in a finger-pull that is configured to be engageble by a finger of a user to assist in removing the clamp from the receiving-channel.

16. The components for forming the primary water tight seal according to claim 1, wherein the clamp has a tab that extends from the clamp that is substantially perpendicular from a major plane of the side wall; wherein the tab snaps onto a corner of the neck-gasket-accommodator.

17. The components for forming the primary water tight seal according to claim 1, wherein the clamp is rigid to semi-rigid.

18. The components for forming the primary water tight seal according to claim 1, wherein a cross-section of the clamp resembles: a closed polygon; a letter "f"; a letter "L"; a letter "J"; or a letter "C".

19. The components for forming the primary water tight seal according to claim 1, wherein the clamp and the vessel neck gasket are removable from the receiving-channel.

* * * * *